(12) United States Patent
Kim et al.

(10) Patent No.: US 12,110,494 B2
(45) Date of Patent: Oct. 8, 2024

(54) METHOD FOR BIOLOGICALLY PRODUCING SUGAR ALCOHOL FROM AGAR

(71) Applicant: Korea University Research and Business Foundation, Seoul (KR)

(72) Inventors: Kyoung Heon Kim, Seoul (KR); Yong Su Jin, Champaign, IL (US); Dong-Hyun Kim, Busan (KR); Eun-Ju Yun, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 870 days.

(21) Appl. No.: 17/273,621

(22) PCT Filed: Sep. 5, 2019

(86) PCT No.: PCT/KR2019/011505
§ 371 (c)(1),
(2) Date: Mar. 4, 2021

(87) PCT Pub. No.: WO2020/050659
PCT Pub. Date: Mar. 12, 2020

(65) Prior Publication Data
US 2022/0220490 A1 Jul. 14, 2022

(30) Foreign Application Priority Data

Sep. 6, 2018 (KR) .................... 10-2018-0106567

(51) Int. Cl.
| | | |
|---|---|---|
| *C12N 15/81* | (2006.01) | |
| *C07K 14/195* | (2006.01) | |
| *C12N 9/24* | (2006.01) | |
| *C12N 9/38* | (2006.01) | |
| *C12P 7/18* | (2006.01) | |

(52) U.S. Cl.
CPC ............ *C12N 15/81* (2013.01); *C07K 14/195* (2013.01); *C12N 9/2471* (2013.01); *C12P 7/18* (2013.01); *C12Y 101/01021* (2013.01); *C12Y 302/01023* (2013.01)

(58) Field of Classification Search
None
See application file for complete search history.

(56) References Cited

FOREIGN PATENT DOCUMENTS

KR 10-2017-0114785 A 10/2017

OTHER PUBLICATIONS

Domingues et al. Appl Microbiol Biotechnol. May 1999; 51(5):621-6.*
GenBank Accession No. X06997 Jul. 25, 2016.*
GenBank Accession No. LT708115 Apr. 28, 2017.*
GenBank Accession No. XM_452194 Sep. 25, 2017.*
GenBank Accession No. AY526090 Feb. 26, 2004.*
GenBank accession No. CP020130 Mar. 21, 2017.*
NCBI BLASTN search of SEQ ID No. 1 retrieved on Feb. 8, 2024.*
Claudio A. Masuda, et al., "Overexpression of the aldose reductase GRE 3 suppresses lithium-induced galactose toxicity in*Saccharomyces cerevisiae*", FEMS Yeast Res, 2008, pp. 1245-1253, vol. 8.
Javier A. Varela, et al., "Polymorphisms in the LAC12 gene explain lactose utilisation variability in Kluyveromyces marxianus strains", FEMS Yeast Research, 2017, pp. 1-13, vol. 17, No. 3.
*Saccharomyces cerevisiae* S288c trifunctional aldehyde reductase/xylose reductase/glucose 1-dehydrogenase (NADP(+)) (GRE3), partial mRNA, NCBI, GenBank, NM_001179234.1, Mar. 15, 2017.
Kluyveromyces lactis LAC12 gene for lactose permease, NCBI, GenBank: X06997.1, Jul. 25, 2016.
Kluyveromyces lactis beta-D-galactosidase (LAC4) gene, complete cds, NCBI, GenBank: M84410.1, Apr. 27, 1993.
International Search Report for PCT/KR2019/011505 dated Jan. 8, 2020 (PCT/ISA/210).

* cited by examiner

*Primary Examiner* — Oluwatosin A Ogunbiyi
(74) *Attorney, Agent, or Firm* — Sughrue Mion, PLLC

(57) ABSTRACT

The present invention relates to a method for biologically producing, from seaweeds, 3,6-anhydro-L-galactitol (L-AHGol) which is a novel sugar alcohol, and agarobititol (ABol) which is in a disaccharide form having 3,6-anhydro-L-galactitol (L-AHGol) as a reducing end, by using a genetic engineering technique in GRAS strains.

12 Claims, 18 Drawing Sheets
Specification includes a Sequence Listing.

[FIG 1]
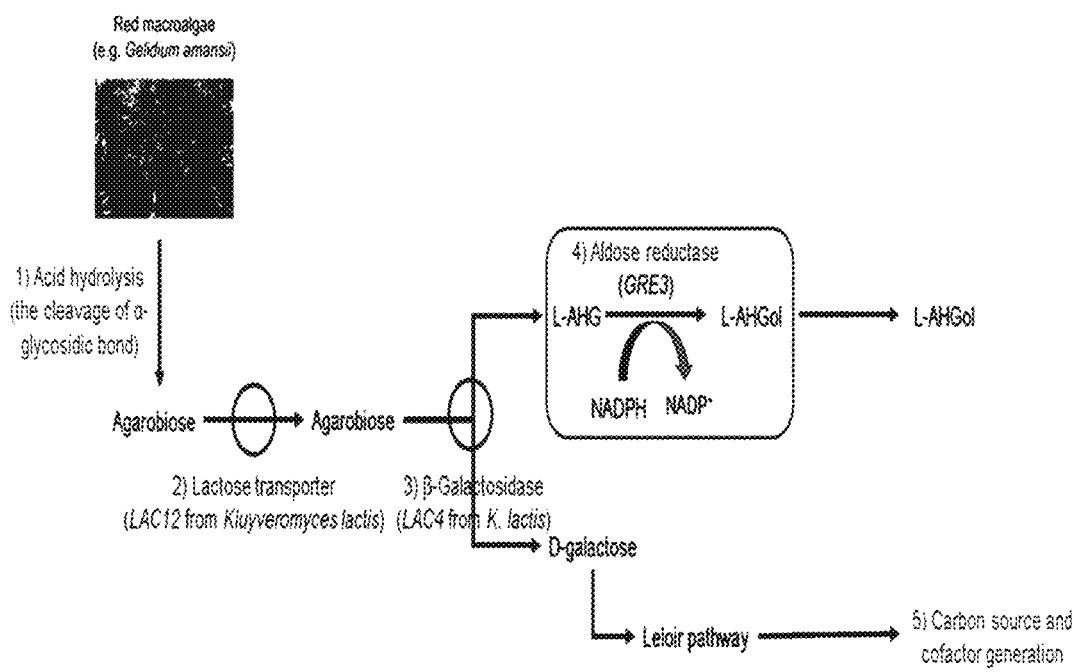

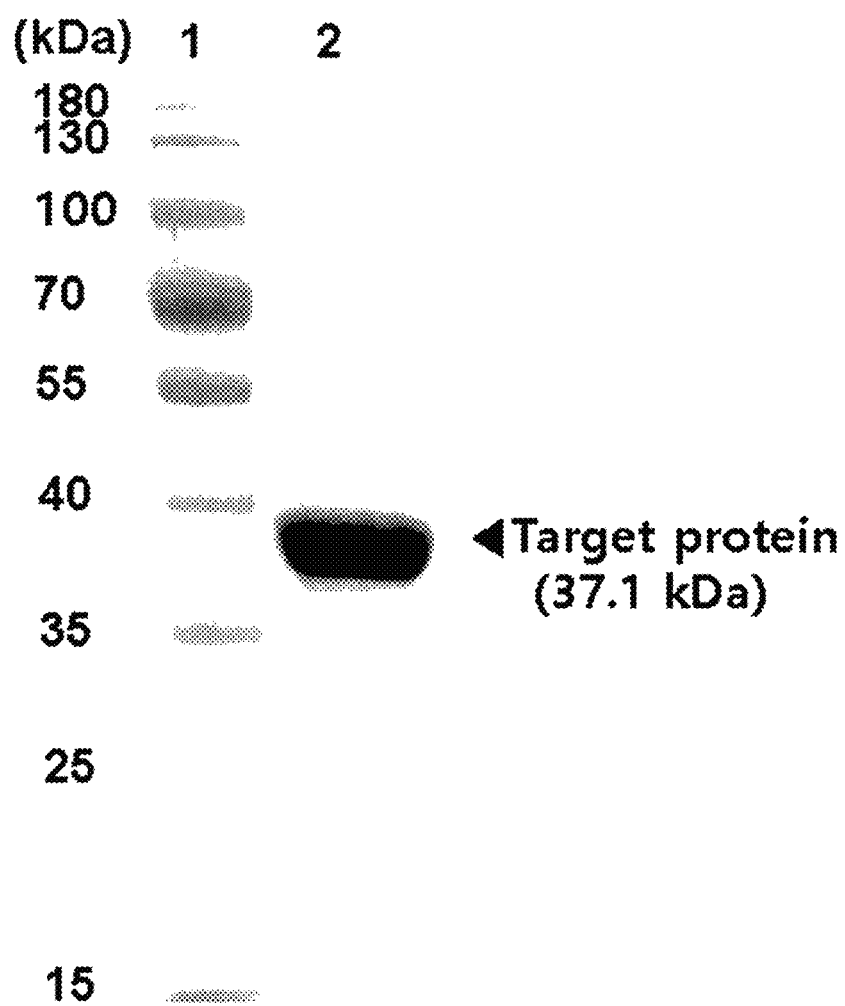
[FIG 2]

[FIG 3A]
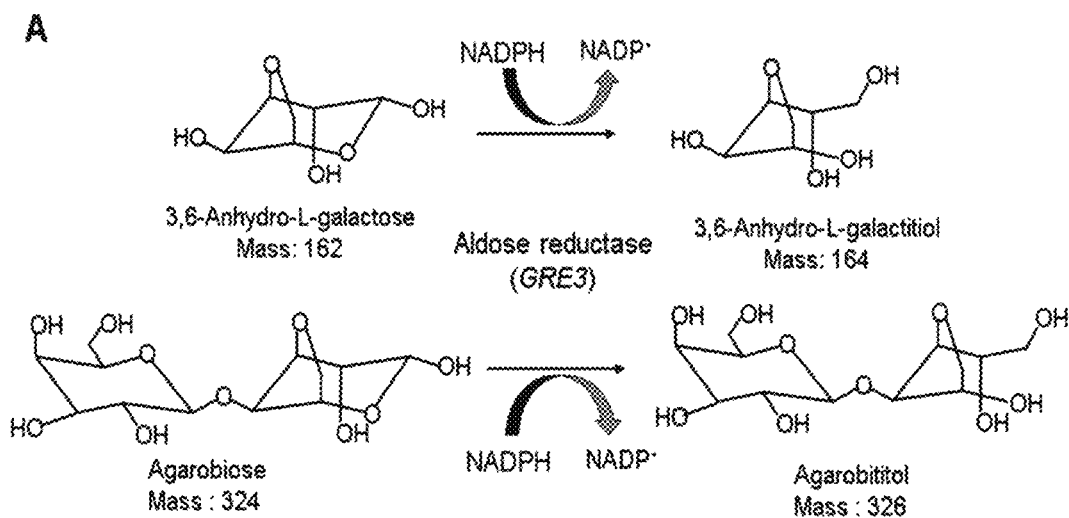
[FIG 3B]
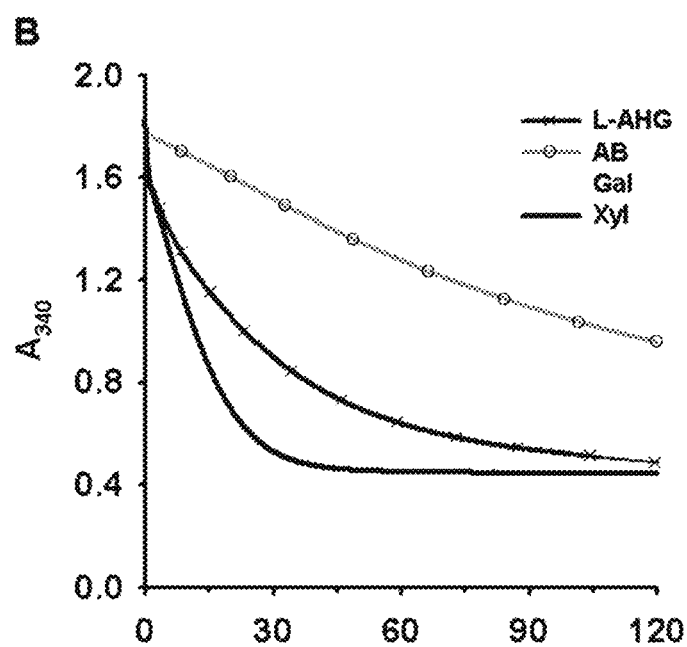

[FIG 3C]
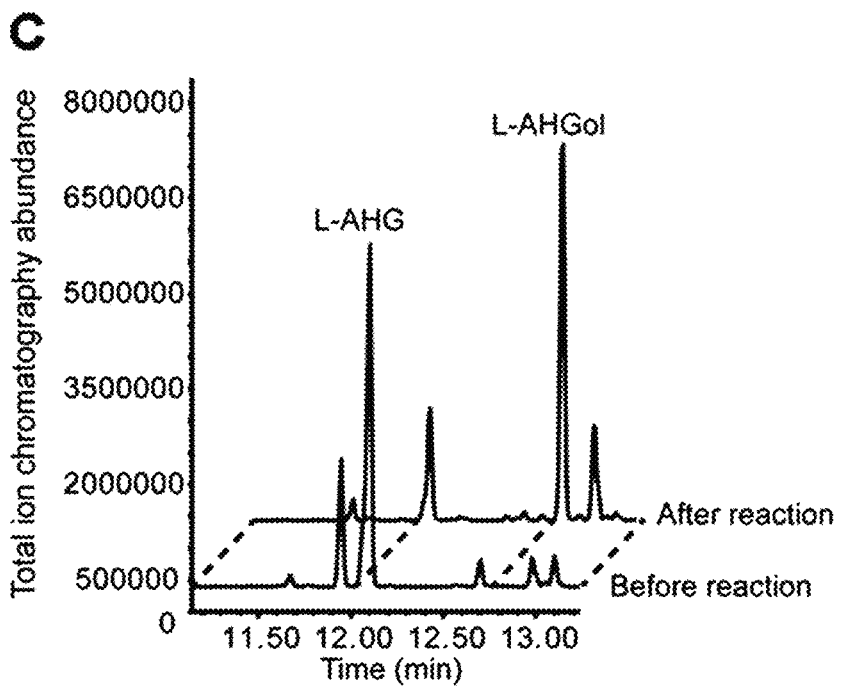
[FIG 3D]
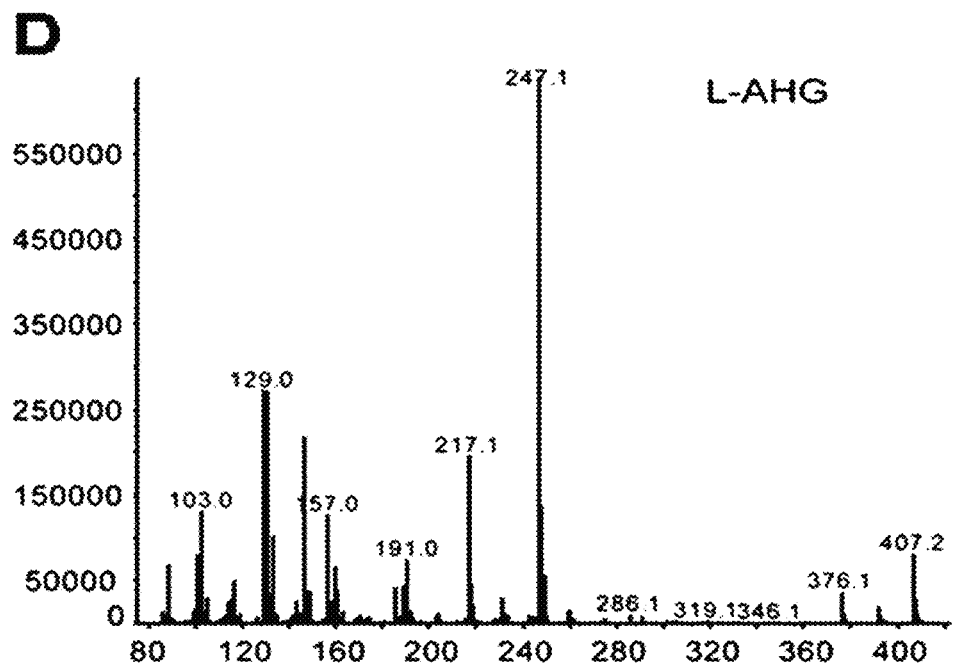

[FIG 3E]
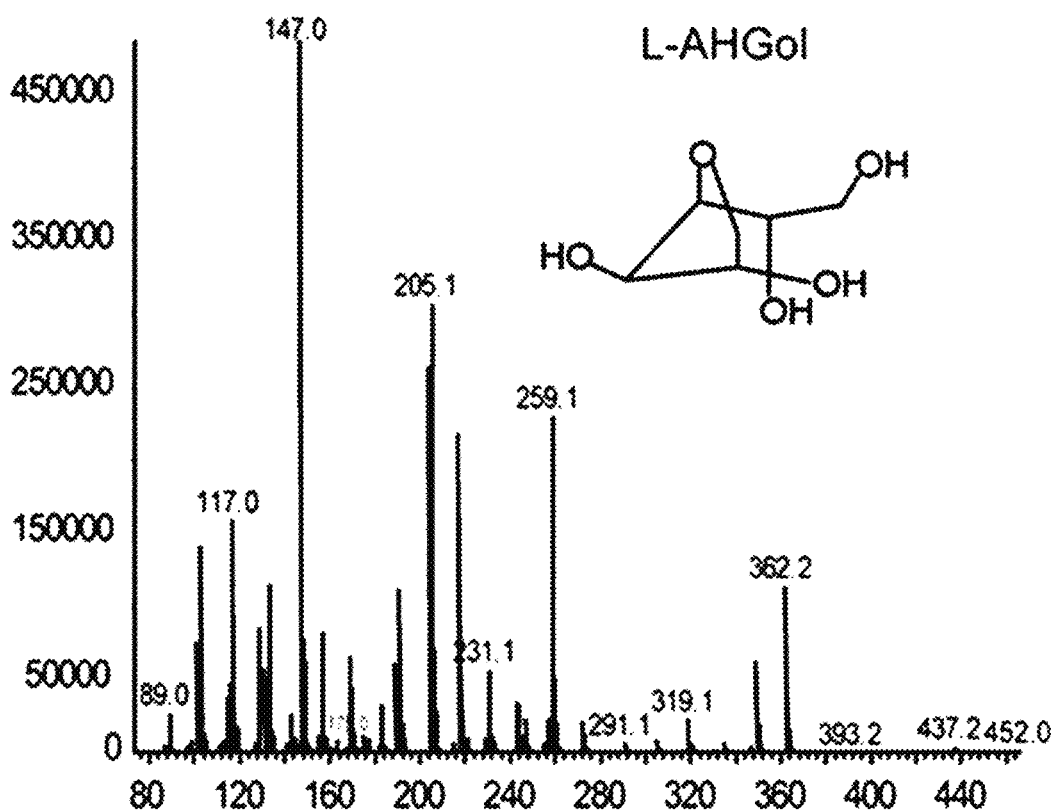
[FIG 3F]
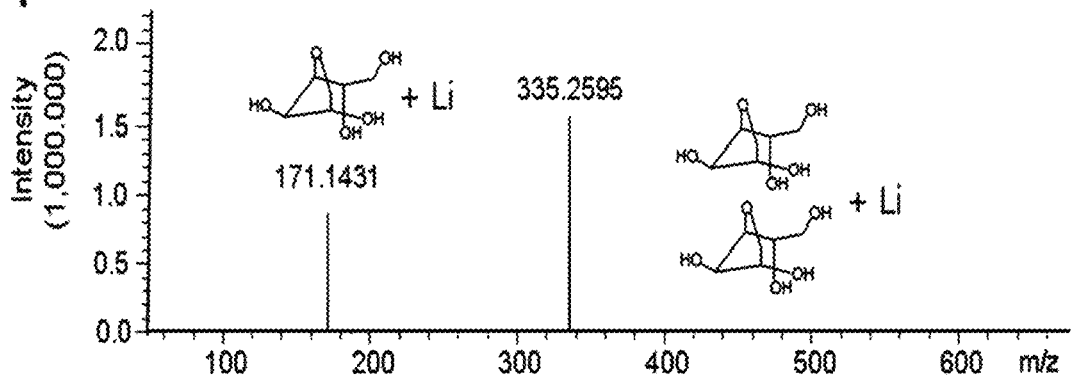

[FIG 3G]
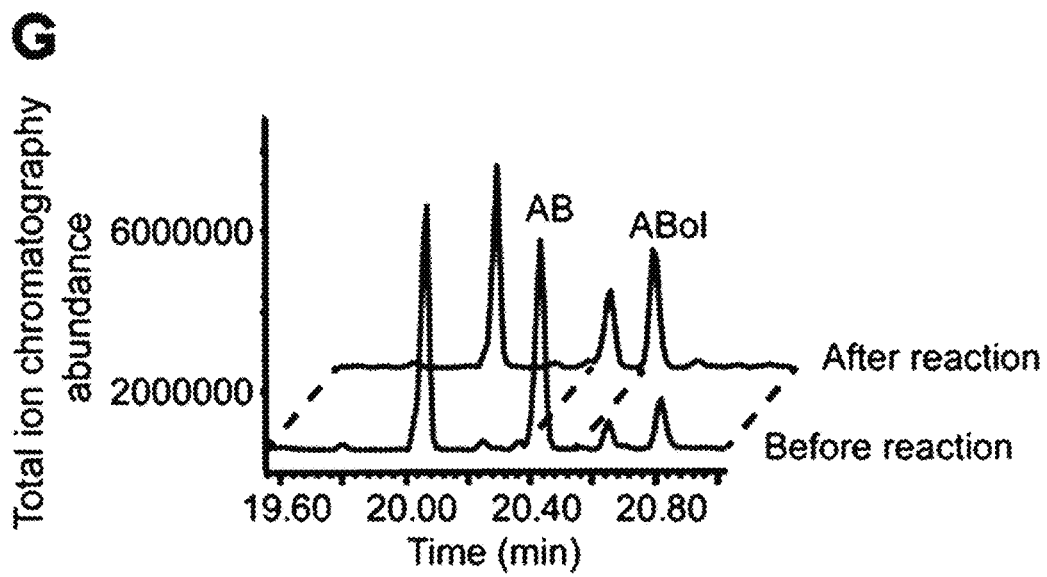
[FIG 3H]
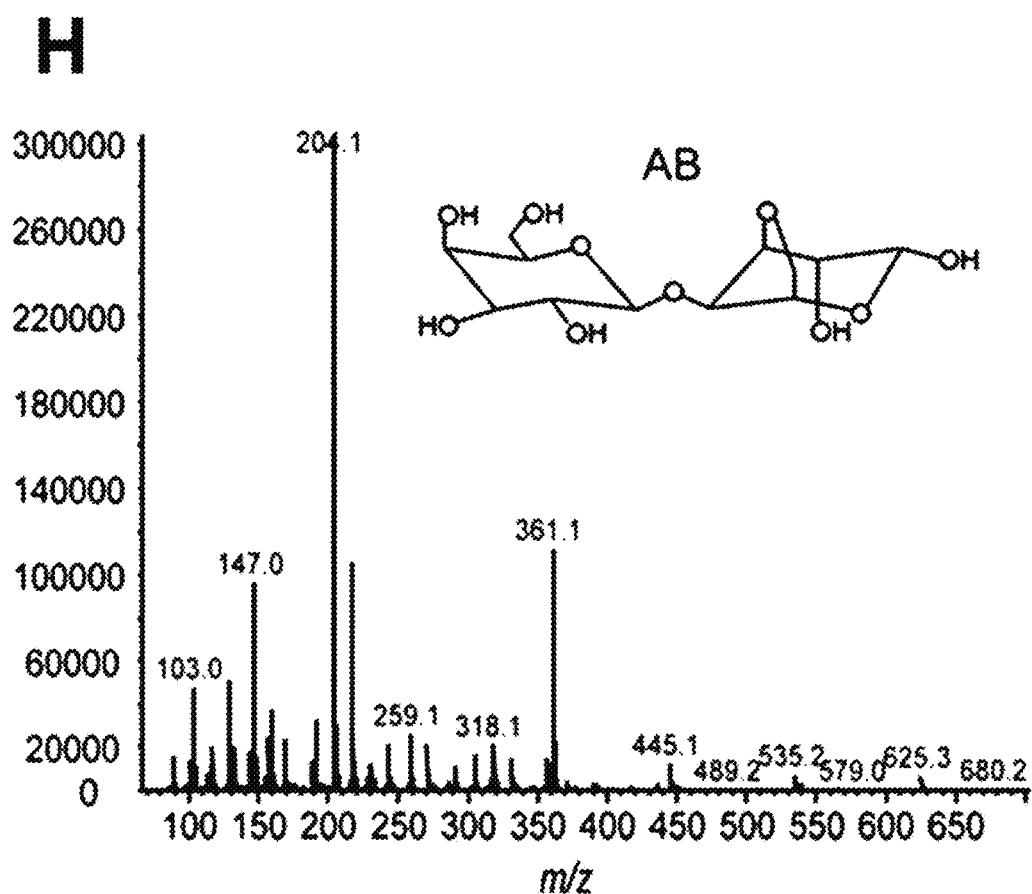

[FIG 3I]
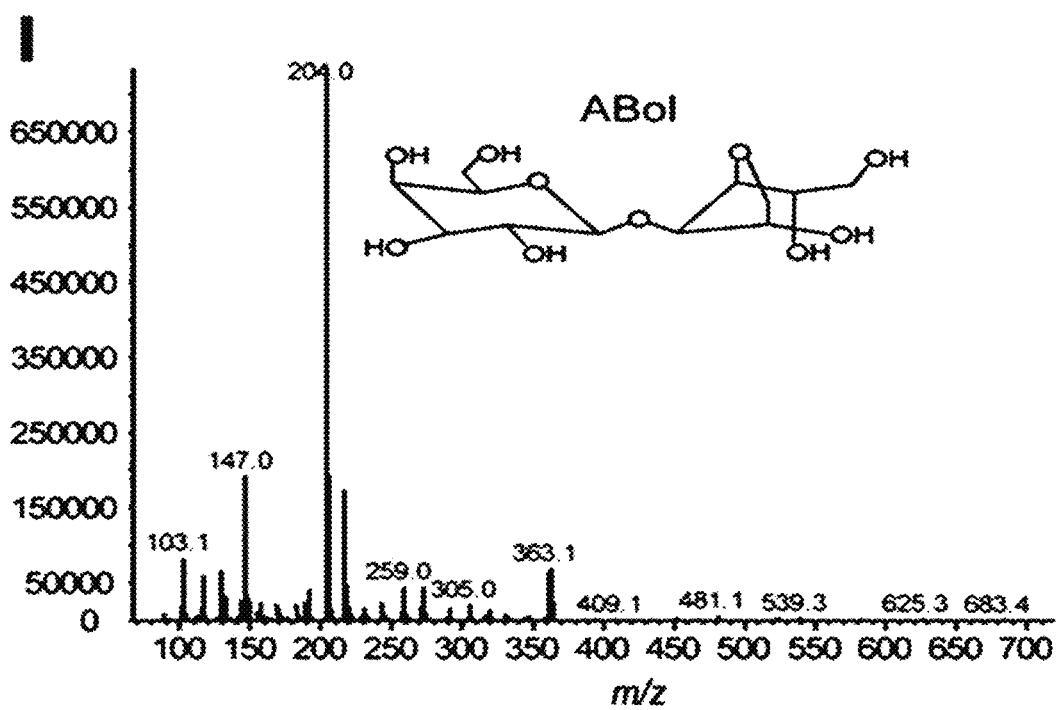
[FIG 3J]
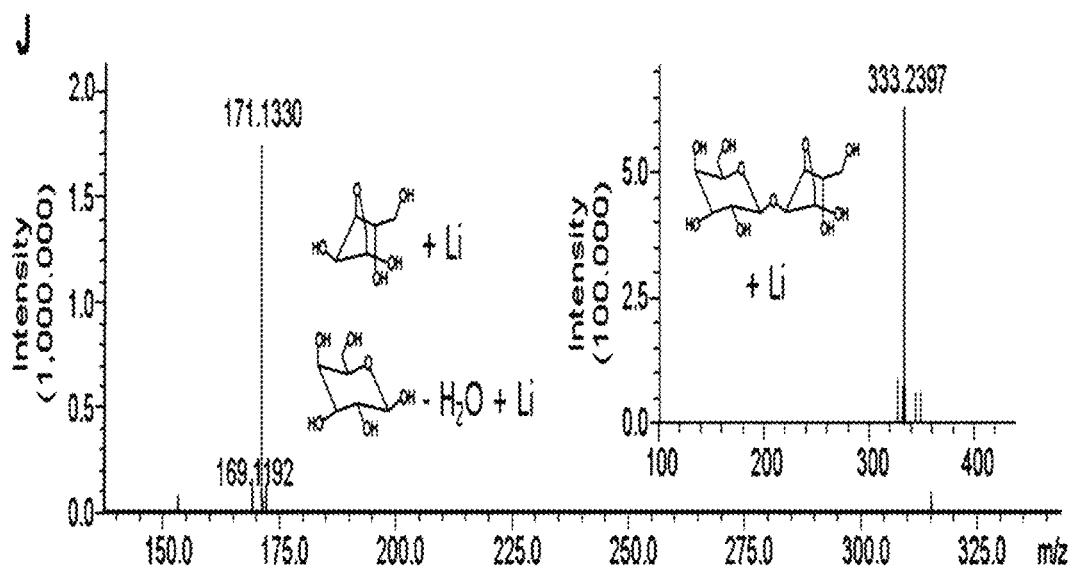

[FIG 4A]
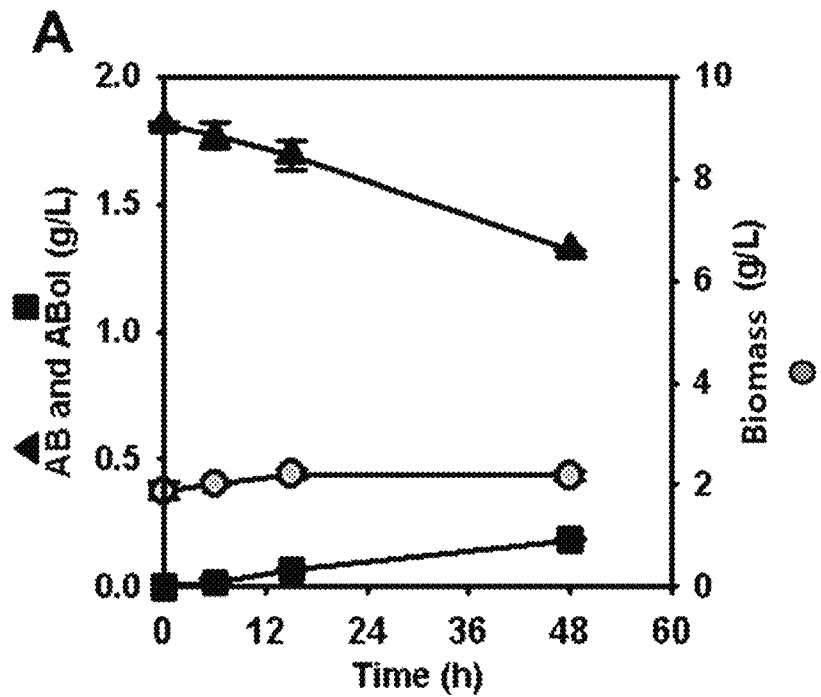
[FIG 4B]
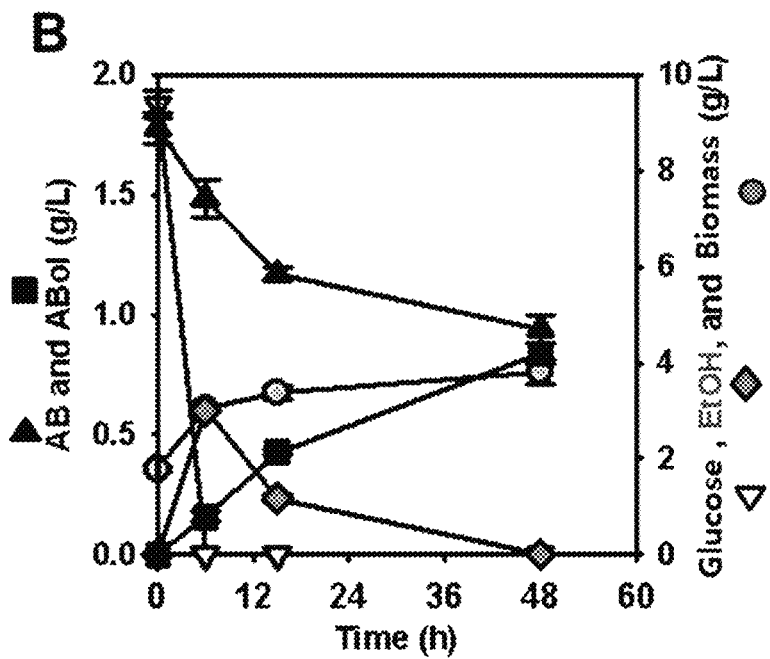

[FIG 4C]
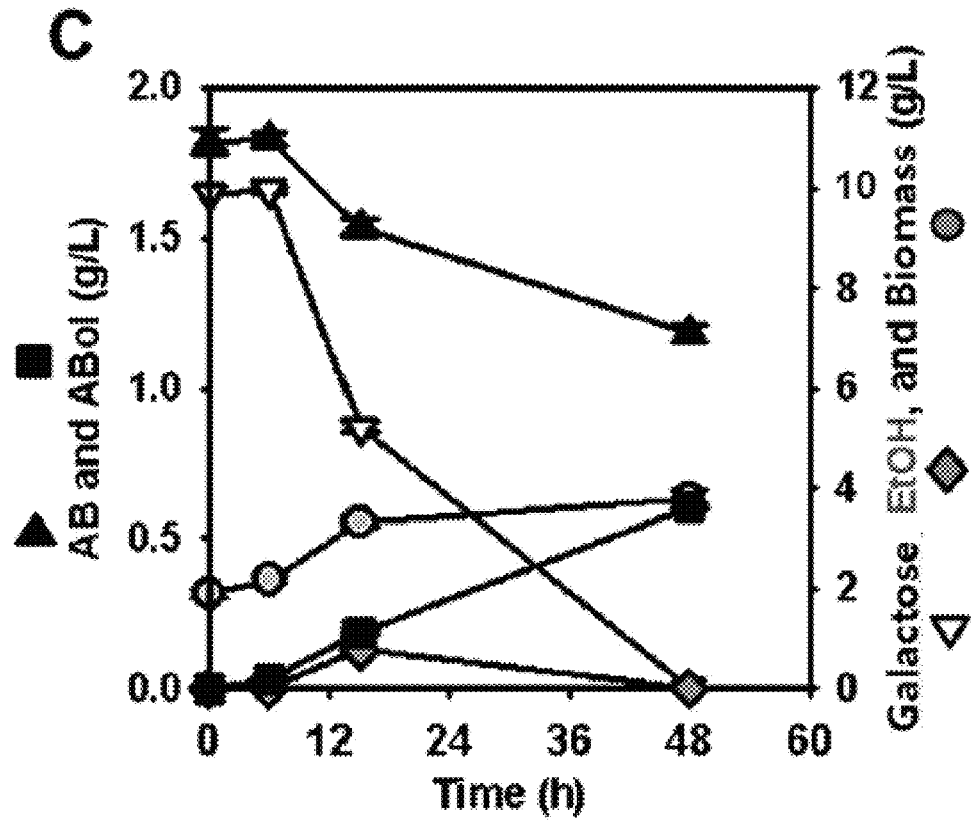
[FIG 4D]
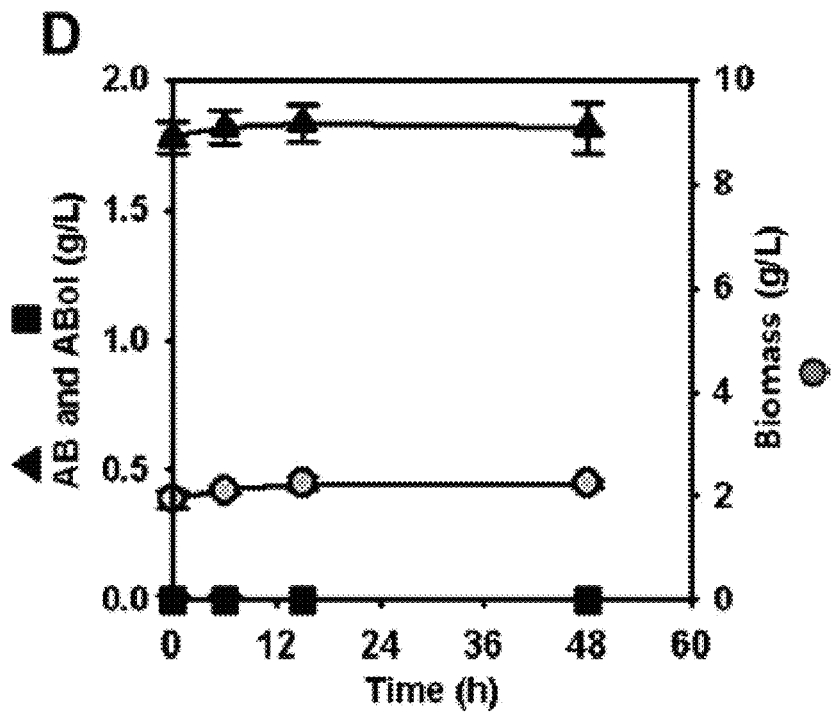

[FIG 4E]
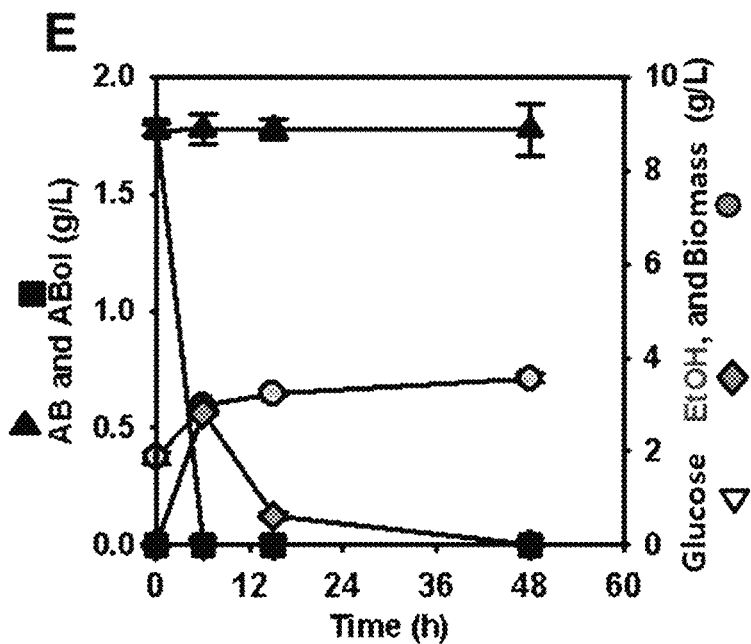
[FIG 4F]
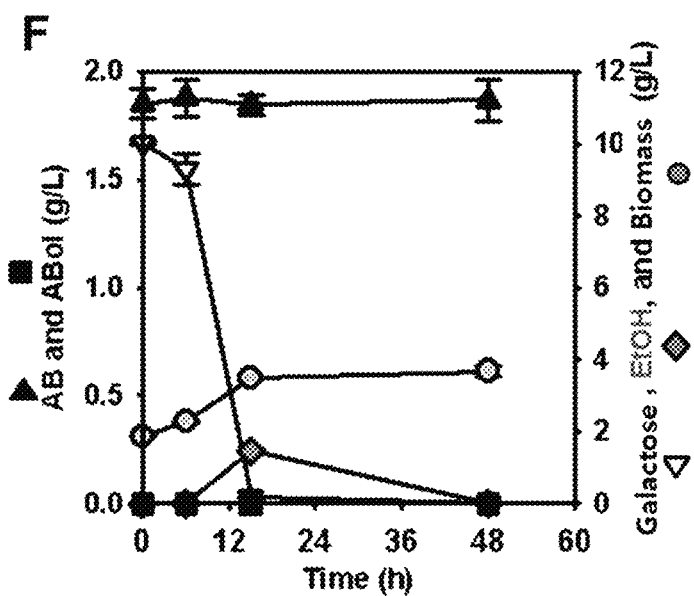

[FIG. 5]
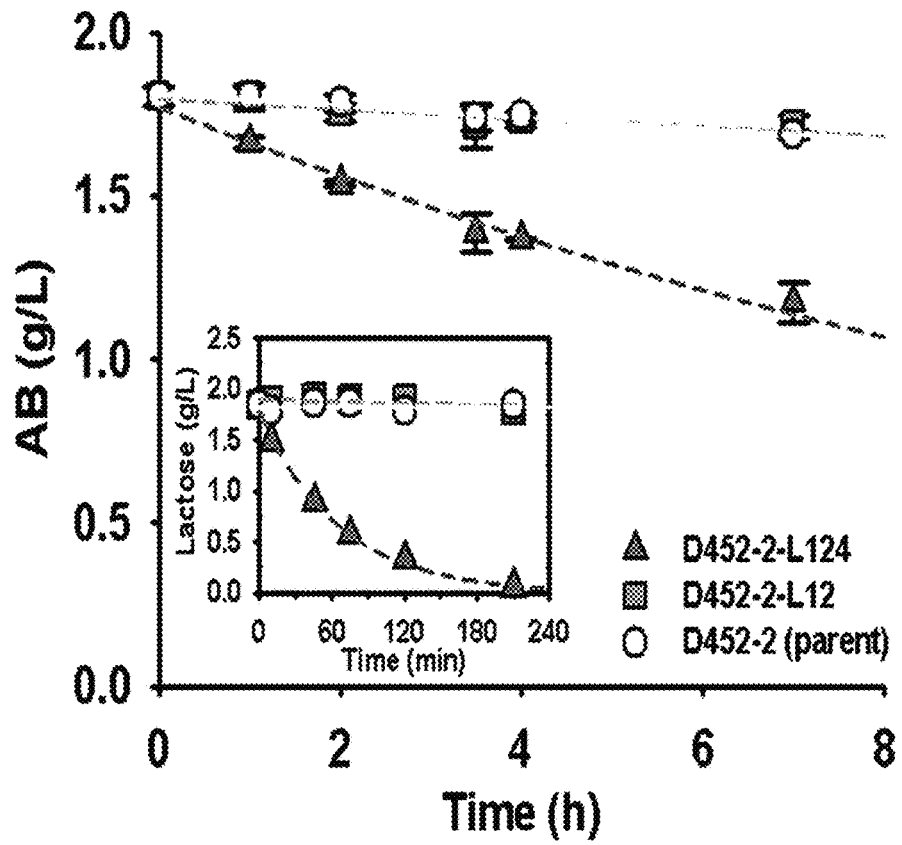
[FIG. 6A]
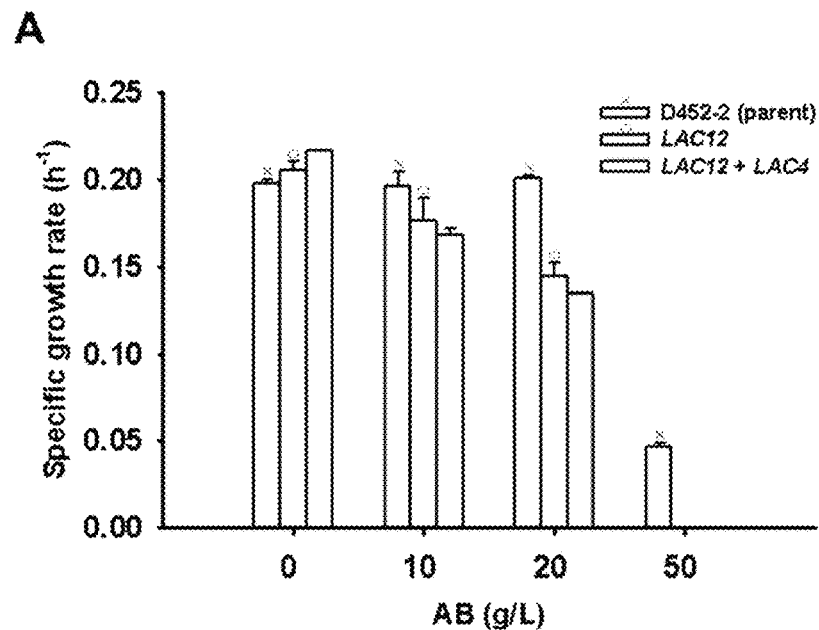

[FIG 6B]
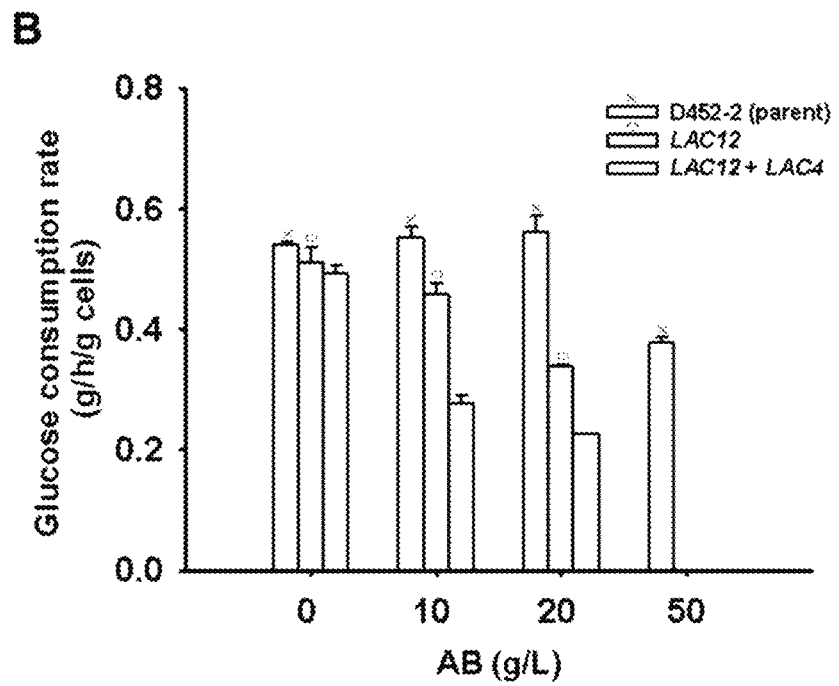
[FIG 7A]
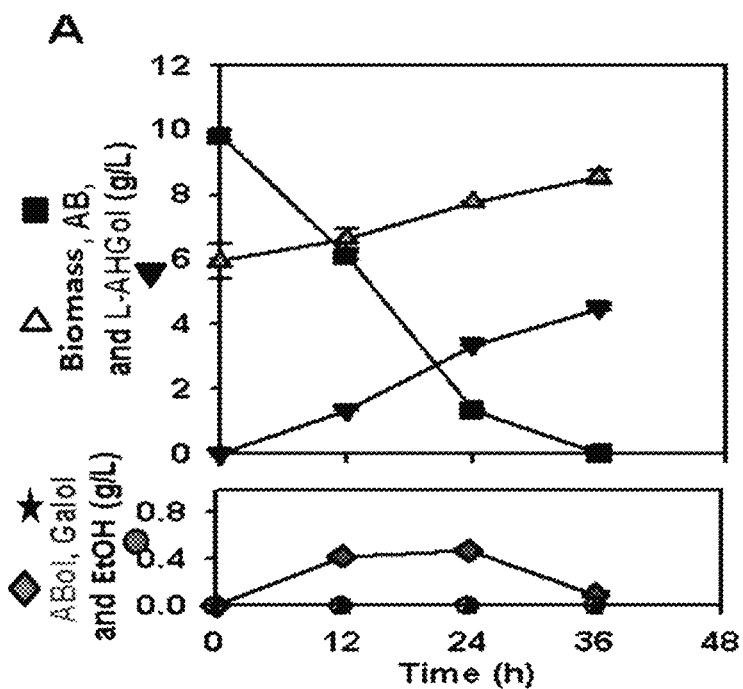

[FIG 7B]
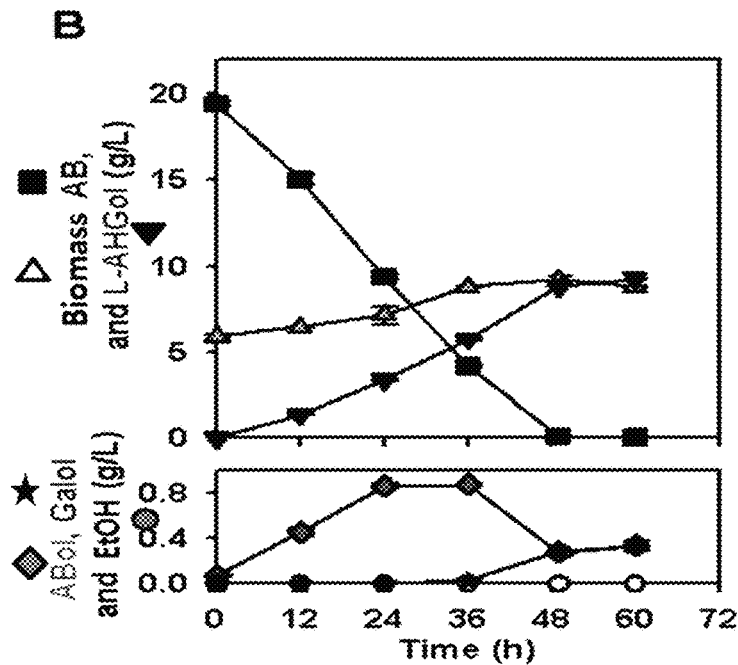
[FIG 7C]
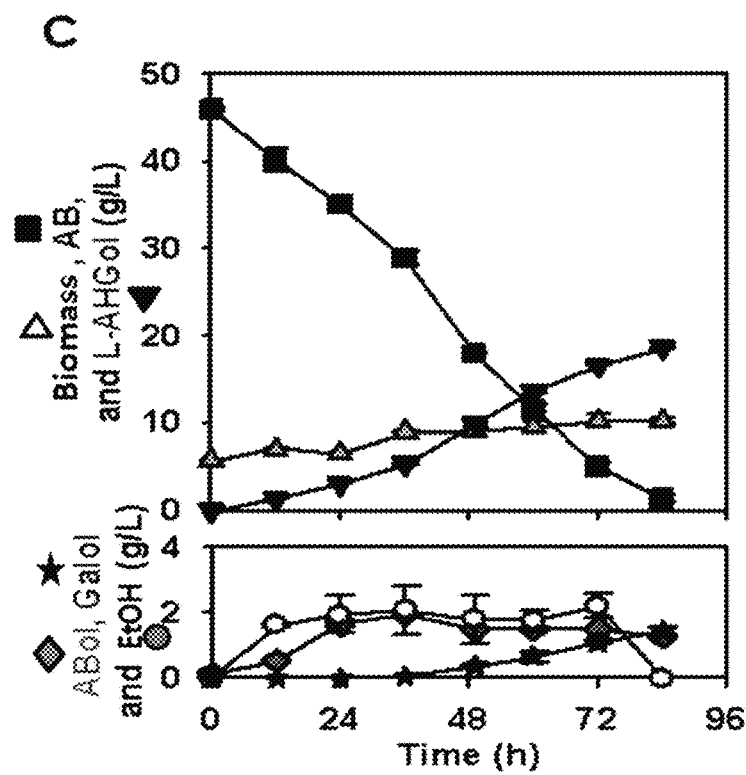

[FIG 7D]
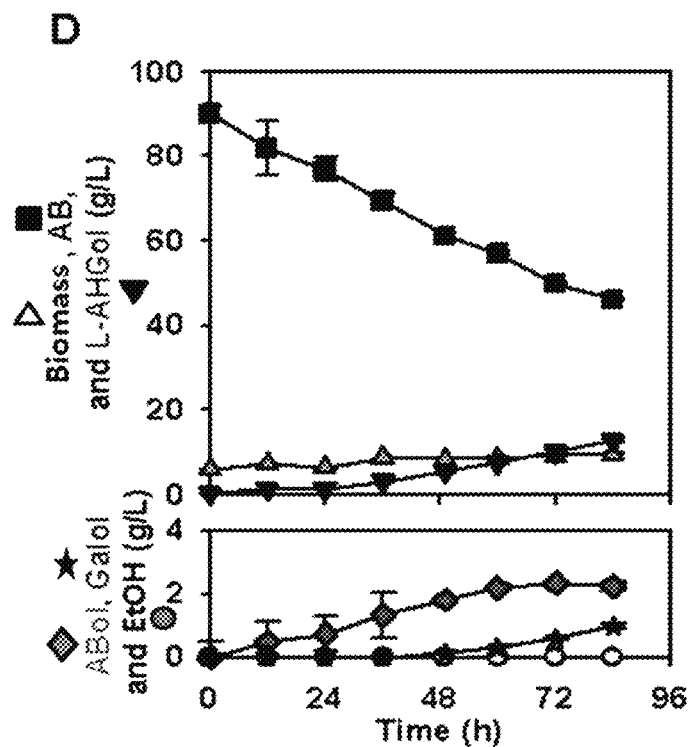
[FIG 8]
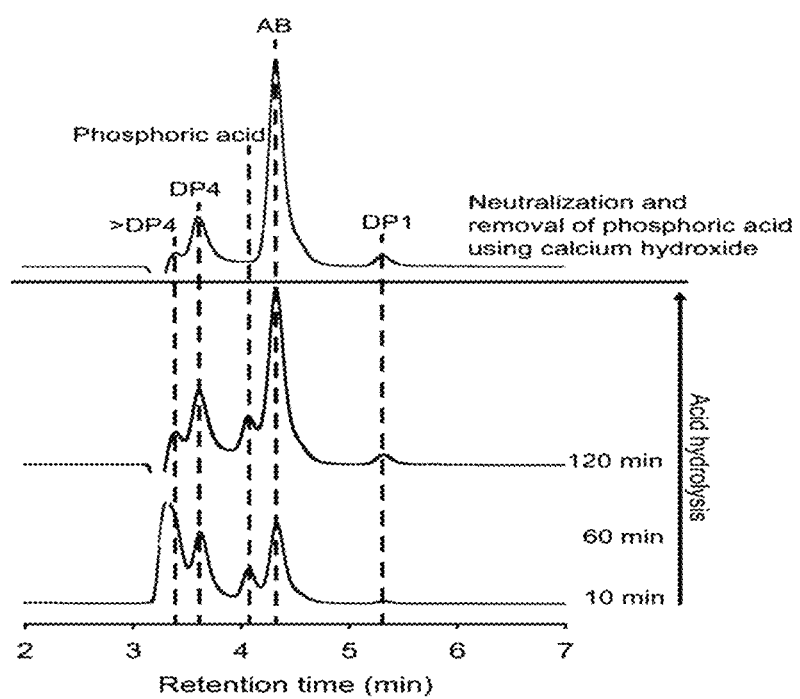

[FIG 9]
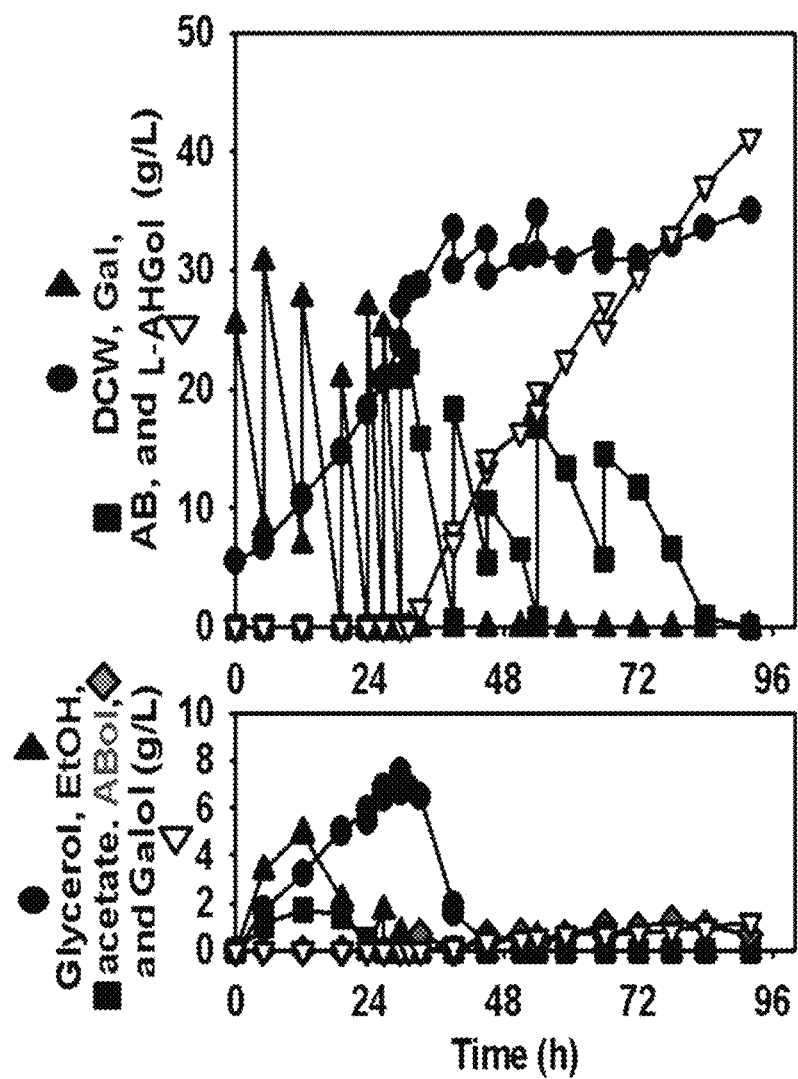

[FIG 10]
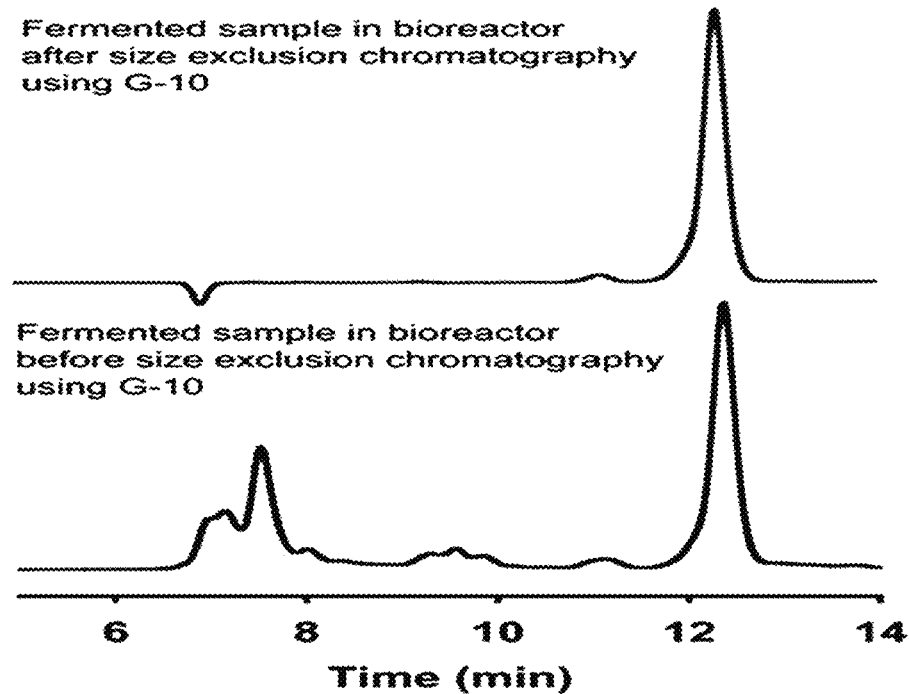
[FIG 11A]
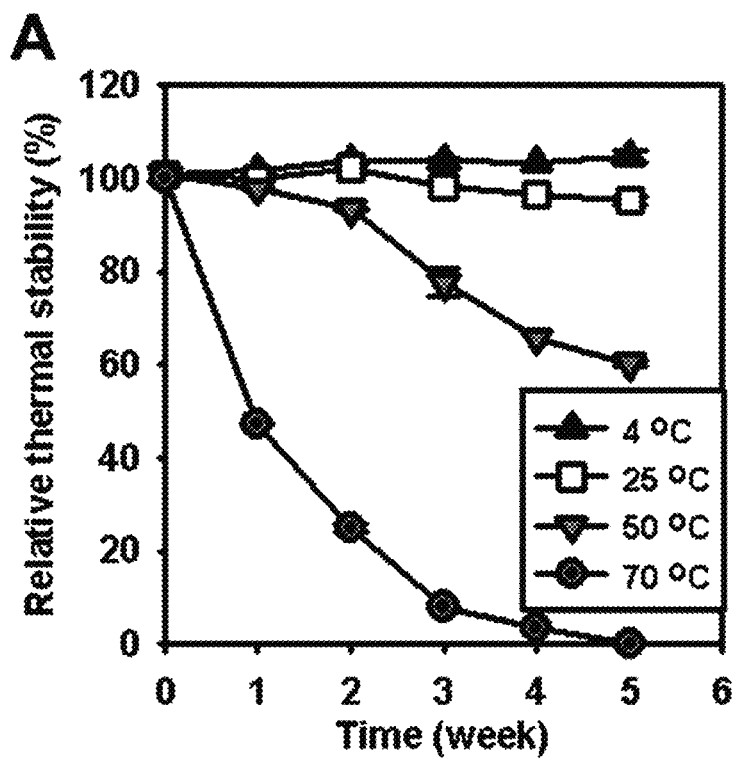

[FIG 11B]
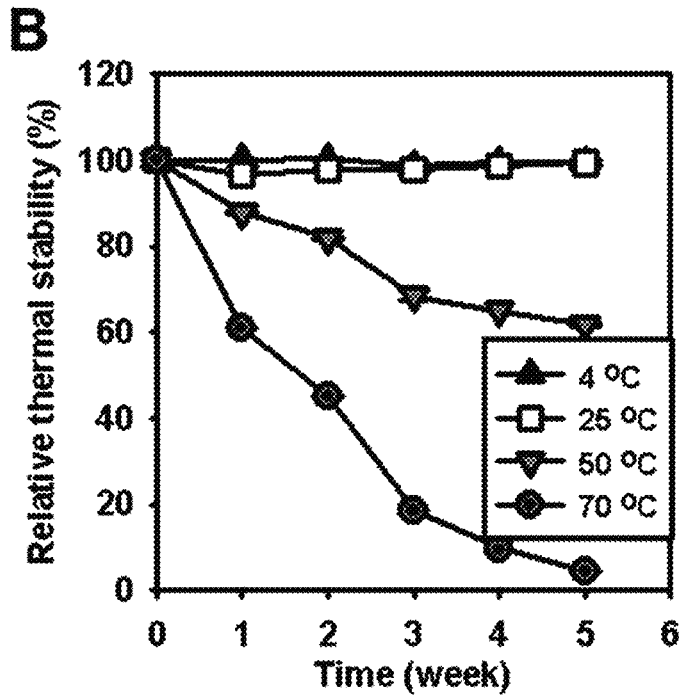
[FIG 11C]
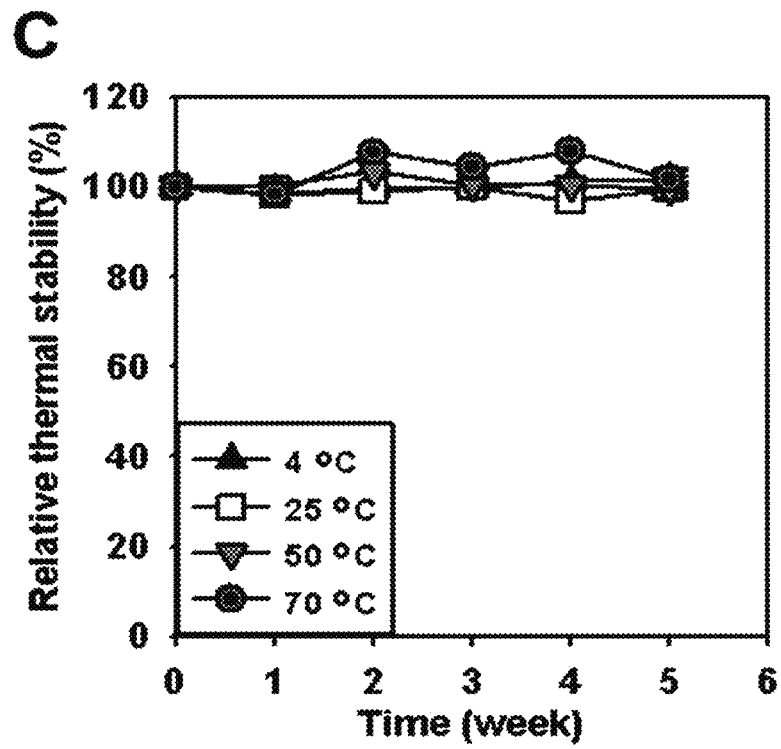

[FIG 11D]
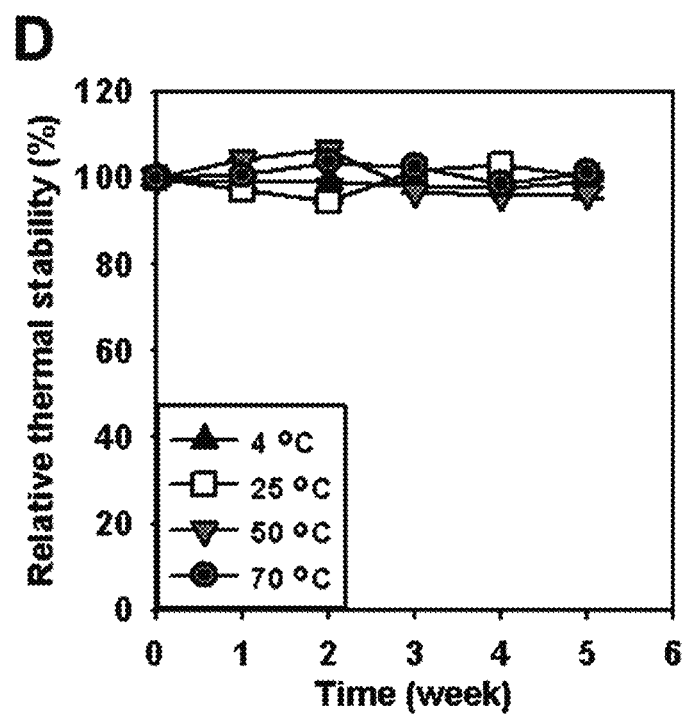

SEQUENCE LISTING

<160> NUMBER OF SEQ ID NOS: 26

<210> SEQ ID NO 1
<211> LENGTH: 984
<212> TYPE: DNA
<213> ORGANISM: Saccharomyces cerevisiae

<400> SEQUENCE: 1

```
atgtcttcac tggttactct taataacggt ctgaaaatgc ccctagtcgg cttagggtgc      60
tggaaaattg acaaaaaagt ctgtgcgaat caaatttatg aagctatcaa attaggctac     120
cgtttattcg atggtgcttg cgactacggc aacgaaaagg aagttggtga aggtatcagg     180
aaagccatct ccgaaggtct tgtttctaga aaggatatat ttgttgtttc aaagttatgg     240
aacaattttc accatcctga tcatgtaaaa ttagctttaa agaagacctt aagcgatatg     300
ggacttgatt atttagacct gtattatatt cacttcccaa tcgccttcaa atatgttcca     360
tttgaagaga aatacctcc aggattctat acgggcgcag atgacgagaa gaaaggtcac      420
atcaccgaag cacatgtacc aatcatagat acgtaccggg ctctggaaga atgtgttgat     480
gaaggcttga ttaagtctat tggtgtttcc aactttcagg gaagcttgat tcaagattta     540
ttacgtggtt gtagaatcaa gcccgtggct ttgcaaattg aacaccatcc ttatttgact     600
caagaacacc tagttgagtt ttgtaaatta cacgatatcc aagtagttgc ttactcctcc     660
ttcggtcctc aatcattcat tgagatggac ttacagttgg caaaaaccac gccaactctg     720
```

```
ttcgagaatg atgtaatcaa aaggtctca caaaaccatc caggcagtac cacttcccaa      780
gtattgctta gatgggcaac tcagagaggc attgccgtca ttccaaaatc ttccaagaag      840
gaaaggttac ttggcaacct agaaatcgaa aaaaagttca ctttaacgga gcaagaattg      900
aaggatattt ctgcactaaa tgccaacatc agatttaatg atccatggac ctggttggat      960
ggtaaattcc ccacttttgc ctga                                             984
```

```
<210> SEQ ID NO 2
<211> LENGTH: 1764
<212> TYPE: DNA
<213> ORGANISM: Kluyveromyces lactis

<400> SEQUENCE: 2
```

```
atggcagatc attcgagcag ctcatcttcg ctgcagaaga agccaattaa tactatcgag       60
cataaagaca ctttgggcaa tgatcgggat cacaaggaag ccttgaacag tgataatgat      120
aatacttctg gattgaaaat caatggtgtc cccatcgagg acgctagaga ggaagtgctc      180
ttaccaggtt acttgtcgaa gcaatattac aaattgtacg gtttatgttt tataacatat      240
ctgtgtgcta ctatgcaagg ttatgatggg gctttaatgg ttctatcta taccgaagat       300 gcatatttga atactacca tttggatatt aactcatcct ctggtactgg tctagtgttc       360
tctattttca cgttggtca aatttgcggt gcattcttg ttcctcttat ggattggaaa       420
ggtagaaaac ctgctatttt aattgggtgt ctgggtgttg ttattggtgc tattatttcg      480
tctttaacaa caacaaagag tgcattaatt ggtggtagat ggtcgtggc cttttttcgct      540 acaatcgcta atgcagcagc tccaacatac tgtgcagaag tggctccagc tcacttaaga      600
ggtaaggttg caggtcttta taacaccctt tggtctgtcg gttccattgt tgctgccttt      660
agcacttacg gtaccaacaa aaacttccct aactcctcca aggctttaa gattccatta      720 tacttacaaa tgatgttccc aggtcttgtg tgtatatttg gttggttaat cccagaatct      780
ccaagatggt tggttggtgt tggccgtgag gaagaagctc gtgaattcat tatcaaatac      840
cacttaaatg gcgatagaac tcatccatta ttggatatgg agatggcaga ataatagaa      900 tctttccatg gtacagattt atcaaaccct ctagaaatgt tagatgtaag gagcttattc      960
agaacgagat cggataggta cagagcaatg ttggttatac ttatggcttg gttcggtcaa     1020
ttttccggta acaatgtgtg ttcgtactat ttgcctacca tgttgagaaa tgttggtatg     1080
aagagtgtct cattgaatgt gttaatgaat ggtgtttat ccatcgtcac ttggatttct     1140
tcaatttgcg gtgcattctt tattgataag attggtagaa gggaaggttt ccttggttct     1200
atctcaggtg ctgcattagc attgacaggt ctatctatct gtactgctcg ttatgagaag     1260
actaagaaga gagtgcttc caatggtgca ttggtgttca tttatctctt tggtggtatc     1320
tttctttttg ctttcactcc aatgcaatcc atgtactcaa cagaagtgtc tacaaacttg     1380
acgagatcta aggcccaact cctcaacttt gtggtttctg tgttgcccca atttgttaat     1440
caatttgcta ctccaaaggc aatgaagaat atcaaatatt ggttctatgt gttctacgtt     1500
ttcttcgata ttttcgaatt tattgttatc tacttcttct tcgttgaaac taagggtaga     1560
agcttagaag aattagaagt tgtctttgaa gctccaaacc caagaaaggc atccgttgat     1620
caagcattct ggctcaagt cagggcaact ttggtccaac gaaatgacgt tagagttgca     1680
aatgctcaaa atttgaaaga gcaagagcct ctaaagagcg atgctgatca tgtcgaaaag     1740
ctttcagagg cagaatctgt ttaa                                            1764
```

<210> SEQ ID NO 3
<211> LENGTH: 3078
<212> TYPE: DNA
<213> ORGANISM: Kluyveromyces lactis

<400> SEQUENCE: 3

| | | | | | |
|---|---|---|---|---|---|
| atgtcttgcc | ttattcctga | gaatttaagg | aaccccaaaa | aggttcacga | aaatagattg | 60 |
| cctactaggg | cttactacta | tgatcaggat | attttcgaat | ctctcaatgg | gccttgggct | 120 |
| tttgcgttgt | ttgatgcacc | tcttgacgct | ccggatgcta | agaatttaga | ctgggaaacg | 180 |
| gcaaagaaat | ggagcaccat | ttctgtgcca | tcccattggg | aacttcagga | agactggaag | 240 |
| tacggtaaac | caatttacac | gaacgtacag | taccctatcc | caatcgacat | cccaaatcct | 300 |
| cccactgtaa | atcctactgg | tgtttatgct | agaacttttg | aattagattc | gaaatcgatt | 360 |
| gagtcgttcg | agcacagatt | gagatttgag | ggtgtggaca | attgttacga | gctttatgtt | 420 |
| aatggtcaat | atgtgggttt | caataagggg | tcccgtaacg | gggctgaatt | tgatatccaa | 480 |
| aagtacgttt | ctgagggcga | aaactagtg | gtcgtcaagg | ttttcaagtg | gtccgattcc | 540 |
| acttatatcg | aggaccaaga | tcaatggtgg | ctctctggta | tttacagaga | cgtttcttta | 600 |
| ctaaaattgc | ctaagaaggc | ccatattgaa | gacgttaggg | tcactacaac | ttttgtggac | 660 |
| tctcagtatc | aggatgcaga | gctttctgtg | aaagttgatg | tccagggttc | ttcttatgat | 720 |
| cacatcaatt | tcacacttta | cgaacctgaa | gatggatcta | agtttacga | tgcaagctct | 780 |
| ttgttgaacg | aggagaatgg | gaacacgact | ttttcaacta | agaatttat | ttccttctcc | 840 |
| accaaaaaga | acgaagaaac | agctttcaag | atcaacgtca | aggccccaga | acattggacc | 900 |
| gcagaaaatc | ctactttgta | caagtaccag | ttggatttaa | ttggatctga | tggcagtgtg | 960 |
| attcaatcta | ttaagcacca | tgttggtttc | agacaagtgg | agttgaagga | cggtaacatt | 1020 |
| actgttaatg | gcaaagacat | tctctttaga | ggtgtcaaca | gacatgatca | ccatccaagg | 1080 |
| ttcggtagag | ctgtgccatt | agattttgtt | gttagggact | tgattctaat | gaagaagttt | 1140 |
| aacatcaatg | ctgttcgtaa | ctcgcattat | ccaaaccatc | ctaaggtgta | tgacctcttc | 1200 |
| gataagctgg | gcttctgggt | cattgacgag | gcagatcttg | aaactcatgg | tgttcaagag | 1260 |
| ccatttaatc | gtcatacgaa | cttggaggct | gaatatccag | atactaaaaa | taaactctac | 1320 |
| gatgttaatg | cccattactt | atcagataat | ccagagtacg | aggtcgcgta | cttagacaga | 1380 |
| gcttcccaac | ttgtcctaag | agatgtcaat | catccttcga | ttattatctg | gtccttgggt | 1440 |
| aacgaagctt | gttatggcag | aaaccacaaa | gccatgtaca | agttaattaa | acaattggat | 1500 |
| cctaccagac | ttgtgcatta | tgagggtgac | ttgaacgctt | tgagtgcaga | tatctttagt | 1560 |
| ttcatgtacc | caacatttga | aattatggaa | aggtggagga | agaaccacac | tgatgaaaat | 1620 |
| ggtaagtttg | aaaagccttt | gatcttgtgt | gagtacggcc | atgcaatggg | taacggtcct | 1680 |
| ggctcttttga | aagaatatca | agagttgttc | tacaaggaga | agttttacca | aggtggcttt | 1740 |
| atctgggaat | gggcaaatca | cggtattgaa | ttcgaagatg | ttagtactgc | agatggtaag | 1800 |
| ttgcataaag | cttatgctta | tggtggtgac | tttaaggaag | aggttcatga | cggagtgttc | 1860 |
| atcatggatg | gtttgtgtaa | cagtgagcat | aatcctactc | cgggccttgt | agagtataag | 1920 |
| aaggttattg | aacccgttca | tattaaaatt | gcgcacggat | ctgtaacaat | cacaaataag | 1980 |
| cacgacttca | ttacgacaga | ccacttattg | tttatcgaca | aggacacggg | aaagacaatc | 2040 |
| gacgttccat | ctttaaagcc | agaagaatct | gttactattc | cttctgatac | aacttatgtt | 2100 |
| gttgccgtgt | tgaaagatga | tgctggtgtt | ctaaaggcag | gtcatgaaat | tgcctggggc | 2160 |

-continued

```
caagctgaac ttccattgaa ggtacccgat tttgttacag agacagcaga aaaagctgcg    2220
aagatcaacg acggtaaacg ttatgtctca gttgaatcca gtggattgca ttttatcttg    2280
gacaaattgt tgggtaaaat tgaaagccta aggtcaagg gtaaggaaat tccagcaag      2340 tttgagggtt cttcaatcac tttctggaga cctccaacga ataatgatga acctaggac    2400 tttaagaact ggaagaagta caatattgat ttaatgaagc aaaacatcca tggagtgagt    2460
gtcgaaaaag gttctaatgg ttctctagct gtagtcacgg ttaactctcg tatatcccca    2520
gttgtatttt actatgggtt tgagactgtt cagaagtaca cgatctttgc taacaaaata    2580
aacttgaaca cttctatgaa gcttactggc gaatatcagc ctcctgattt cccaagagtt    2640
gggtacgaat tctggctagg agatagttat gaatcatttg aatggttagg tcgcgggccc    2700
ggcgaatcat atccggataa gaaggaatct caaagattcg gtctttacga ttccaaagat    2760
gtagaggaat tcgtatatga ctatcctcaa gaaaatggaa atcatacaga tacccacttt    2820
ttgaacatca aatttgaagg tgcaggaaaa ctatcgatct tccaaaagga gaagccattt    2880
aacttcaaga tttcagacga atacggggtt gatgaagctg cccacgcttg tgacgttaaa    2940
agatacggca gacactatct aaggttggac catgcaatcc atggtgttgg tagcgaagca    3000
tgcggacctg ctgttctgga ccagtacaga ttgaaagctc aagatttcaa ctttgagttt    3060
gatctcgctt ttgaataa                                                  3078
```

<210> SEQ ID NO 4
<211> LENGTH: 327
<212> TYPE: PRT
<213> ORGANISM: Saccharomyces cerevisiae

<400> SEQUENCE: 4

```
Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205
```

```
Lys Leu His Asp Ile Gln Val Ala Tyr Ser Ser Phe Gly Pro Gln
210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 5
<211> LENGTH: 587
<212> TYPE: PRT
<213> ORGANISM: Kluyveromyces lactis

<400> SEQUENCE: 5

Met Ala Asp His Ser Ser Ser Ser Ser Leu Gln Lys Lys Pro Ile
1               5                   10                  15

Asn Thr Ile Glu His Lys Asp Thr Leu Gly Asn Asp Arg Asp His Lys
                20                  25                  30

Glu Ala Leu Asn Ser Asp Asn Asp Thr Ser Gly Leu Lys Ile Asn
            35                  40                  45

Gly Val Pro Ile Glu Asp Ala Arg Glu Glu Val Leu Leu Pro Gly Tyr
        50                  55                  60

Leu Ser Lys Gln Tyr Tyr Lys Leu Tyr Gly Leu Cys Phe Ile Thr Tyr
65                  70                  75                  80

Leu Cys Ala Thr Met Gln Gly Tyr Asp Gly Ala Leu Met Gly Ser Ile
                85                  90                  95

Tyr Thr Glu Asp Ala Tyr Leu Lys Tyr His Leu Asp Ile Asn Ser
                100                 105                 110

Ser Ser Gly Thr Gly Leu Val Phe Ser Ile Phe Asn Val Gly Gln Ile
            115                 120                 125

Cys Gly Ala Phe Phe Val Pro Leu Met Asp Trp Lys Gly Arg Lys Pro
        130                 135                 140

Ala Ile Leu Ile Gly Cys Leu Gly Val Val Ile Gly Ala Ile Ile Ser
145                 150                 155                 160

Ser Leu Thr Thr Thr Lys Ser Ala Leu Ile Gly Gly Arg Trp Phe Val
                165                 170                 175

Ala Phe Phe Ala Thr Ile Ala Asn Ala Ala Pro Thr Tyr Cys Ala
                180                 185                 190

Glu Val Ala Pro Ala His Leu Arg Gly Lys Val Ala Gly Leu Tyr Asn
            195                 200                 205

Thr Leu Trp Ser Val Gly Ser Ile Val Ala Ala Phe Ser Thr Tyr Gly
        210                 215                 220

Thr Asn Lys Asn Phe Pro Asn Ser Ser Lys Ala Phe Lys Ile Pro Leu
225                 230                 235                 240

Tyr Leu Gln Met Met Phe Pro Gly Leu Val Cys Ile Phe Gly Trp Leu
```

```
            245                 250                 255
Ile Pro Glu Ser Pro Arg Trp Leu Val Gly Val Gly Arg Glu Glu
            260                 265                 270

Ala Arg Glu Phe Ile Ile Lys Tyr His Leu Asn Gly Asp Arg Thr His
            275                 280                 285

Pro Leu Leu Asp Met Glu Met Ala Glu Ile Ile Glu Ser Phe His Gly
            290                 295                 300

Thr Asp Leu Ser Asn Pro Leu Glu Met Leu Asp Val Arg Ser Leu Phe
305                 310                 315                 320

Arg Thr Arg Ser Asp Arg Tyr Arg Ala Met Leu Val Ile Leu Met Ala
                325                 330                 335

Trp Phe Gly Gln Phe Ser Gly Asn Asn Val Cys Ser Tyr Tyr Leu Pro
            340                 345                 350

Thr Met Leu Arg Asn Val Gly Met Lys Ser Val Ser Leu Asn Val Leu
            355                 360                 365

Met Asn Gly Val Tyr Ser Ile Val Thr Trp Ile Ser Ser Ile Cys Gly
            370                 375                 380

Ala Phe Phe Ile Asp Lys Ile Gly Arg Arg Glu Gly Phe Leu Gly Ser
385                 390                 395                 400

Ile Ser Gly Ala Ala Leu Ala Leu Thr Gly Leu Ser Ile Cys Thr Ala
                405                 410                 415

Arg Tyr Glu Lys Thr Lys Lys Ser Ala Ser Asn Gly Ala Leu Val
            420                 425                 430

Phe Ile Tyr Leu Phe Gly Gly Ile Phe Ser Phe Ala Phe Thr Pro Met
                435                 440                 445

Gln Ser Met Tyr Ser Thr Glu Val Ser Thr Asn Leu Thr Arg Ser Lys
450                 455                 460

Ala Gln Leu Leu Asn Phe Val Ser Gly Val Ala Gln Phe Val Asn
465                 470                 475                 480

Gln Phe Ala Thr Pro Lys Ala Met Lys Asn Ile Lys Tyr Trp Phe Tyr
                485                 490                 495

Val Phe Tyr Val Phe Phe Asp Ile Phe Glu Phe Ile Val Ile Tyr Phe
            500                 505                 510

Phe Phe Val Glu Thr Lys Gly Arg Ser Leu Glu Glu Leu Glu Val Val
        515                 520                 525

Phe Glu Ala Pro Asn Pro Arg Lys Ala Ser Val Asp Gln Ala Phe Leu
        530                 535                 540

Ala Gln Val Arg Ala Thr Leu Val Gln Arg Asn Asp Val Arg Val Ala
545                 550                 555                 560

Asn Ala Gln Asn Leu Lys Glu Gln Glu Pro Leu Lys Ser Asp Ala Asp
                565                 570                 575

His Val Glu Lys Leu Ser Glu Ala Glu Ser Val
            580                 585

<210> SEQ ID NO 6
<211> LENGTH: 1025
<212> TYPE: PRT
<213> ORGANISM: Kluyveromyces lactis

<400> SEQUENCE: 6

Met Ser Cys Leu Ile Pro Glu Asn Leu Arg Asn Pro Lys Lys Val His
1               5                   10                  15

Glu Asn Arg Leu Pro Thr Arg Ala Tyr Tyr Tyr Asp Gln Asp Ile Phe
            20                  25                  30
```

-continued

Glu Ser Leu Asn Gly Pro Trp Ala Phe Ala Leu Phe Asp Ala Pro Leu
         35                  40                  45

Asp Ala Pro Asp Ala Lys Asn Leu Asp Trp Glu Thr Ala Lys Lys Trp
 50                  55                  60

Ser Thr Ile Ser Val Pro Ser His Trp Glu Leu Gln Glu Asp Trp Lys
 65                  70                  75                  80

Tyr Gly Lys Pro Ile Tyr Thr Asn Val Gln Tyr Pro Ile Pro Ile Asp
                 85                  90                  95

Ile Pro Asn Pro Pro Thr Val Asn Pro Thr Gly Val Tyr Ala Arg Thr
            100                 105                 110

Phe Glu Leu Asp Ser Lys Ser Ile Glu Ser Phe Glu His Arg Leu Arg
        115                 120                 125

Phe Glu Gly Val Asp Asn Cys Tyr Glu Leu Tyr Val Asn Gly Gln Tyr
    130                 135                 140

Val Gly Phe Asn Lys Gly Ser Arg Asn Gly Ala Glu Phe Asp Ile Gln
145                 150                 155                 160

Lys Tyr Val Ser Glu Gly Glu Asn Leu Val Val Lys Val Phe Lys
                165                 170                 175

Trp Ser Asp Ser Thr Tyr Ile Glu Asp Gln Asp Gln Trp Trp Leu Ser
            180                 185                 190

Gly Ile Tyr Arg Asp Val Ser Leu Leu Lys Leu Pro Lys Lys Ala His
        195                 200                 205

Ile Glu Asp Val Arg Val Thr Thr Phe Val Asp Ser Gln Tyr Gln
    210                 215                 220

Asp Ala Glu Leu Ser Val Lys Val Asp Val Gln Gly Ser Ser Tyr Asp
225                 230                 235                 240

His Ile Asn Phe Thr Leu Tyr Glu Pro Glu Asp Gly Ser Lys Val Tyr
                245                 250                 255

Asp Ala Ser Ser Leu Leu Asn Glu Glu Asn Gly Asn Thr Thr Phe Ser
            260                 265                 270

Thr Lys Glu Phe Ile Ser Phe Ser Thr Lys Lys Asn Glu Glu Thr Ala
        275                 280                 285

Phe Lys Ile Asn Val Lys Ala Pro Glu His Trp Thr Ala Glu Asn Pro
    290                 295                 300

Thr Leu Tyr Lys Tyr Gln Leu Asp Leu Ile Gly Ser Asp Gly Ser Val
305                 310                 315                 320

Ile Gln Ser Ile Lys His His Val Gly Phe Arg Gln Val Glu Leu Lys
                325                 330                 335

Asp Gly Asn Ile Thr Val Asn Gly Lys Asp Ile Leu Phe Arg Gly Val
            340                 345                 350

Asn Arg His Asp His His Pro Arg Phe Gly Arg Ala Val Pro Leu Asp
        355                 360                 365

Phe Val Val Arg Asp Leu Ile Leu Met Lys Lys Phe Asn Ile Asn Ala
    370                 375                 380

Val Arg Asn Ser His Tyr Pro Asn His Pro Lys Val Tyr Asp Leu Phe
385                 390                 395                 400

Asp Lys Leu Gly Phe Trp Val Ile Asp Glu Ala Asp Leu Glu Thr His
                405                 410                 415

Gly Val Gln Glu Pro Phe Asn Arg His Thr Asn Leu Glu Ala Glu Tyr
            420                 425                 430

Pro Asp Thr Lys Asn Lys Leu Tyr Asp Val Asn Ala His Tyr Leu Ser
        435                 440                 445

Asp Asn Pro Glu Tyr Glu Val Ala Tyr Leu Asp Arg Ala Ser Gln Leu

```
                450             455             460
    Val Leu Arg Asp Val Asn His Pro Ser Ile Ile Ile Trp Ser Leu Gly
    465             470             475             480

Asn Glu Ala Cys Tyr Gly Arg Asn His Lys Ala Met Tyr Lys Leu Ile
                    485             490             495

Lys Gln Leu Asp Pro Thr Arg Leu Val His Tyr Glu Gly Asp Leu Asn
                500             505             510

Ala Leu Ser Ala Asp Ile Phe Ser Phe Met Tyr Pro Thr Phe Glu Ile
                515             520             525

Met Glu Arg Trp Arg Lys Asn His Thr Asp Glu Asn Gly Lys Phe Glu
                530             535             540

Lys Pro Leu Ile Leu Cys Glu Tyr Gly His Ala Met Gly Asn Gly Pro
    545             550             555             560

Gly Ser Leu Lys Glu Tyr Gln Glu Leu Phe Tyr Lys Glu Lys Phe Tyr
                    565             570             575

Gln Gly Gly Phe Ile Trp Glu Trp Ala Asn His Gly Ile Glu Phe Glu
                    580             585             590

Asp Val Ser Thr Ala Asp Gly Lys Leu His Lys Ala Tyr Ala Tyr Gly
                    595             600             605

Gly Asp Phe Lys Glu Glu Val His Asp Gly Val Phe Ile Met Asp Gly
                610             615             620

Leu Cys Asn Ser Glu His Asn Pro Thr Pro Gly Leu Val Glu Tyr Lys
    625             630             635             640

Lys Val Ile Glu Pro Val His Ile Lys Ile Ala His Gly Ser Val Thr
                    645             650             655

Ile Thr Asn Lys His Asp Phe Ile Thr Thr Asp His Leu Leu Phe Ile
                    660             665             670

Asp Lys Asp Thr Gly Lys Thr Ile Asp Val Pro Ser Leu Lys Pro Glu
                675             680             685

Glu Ser Val Thr Ile Pro Ser Asp Thr Thr Tyr Val Val Ala Val Leu
                690             695             700

Lys Asp Asp Ala Gly Val Leu Lys Ala Gly His Glu Ile Ala Trp Gly
    705             710             715             720

Gln Ala Glu Leu Pro Leu Lys Val Pro Asp Phe Val Thr Glu Thr Ala
                    725             730             735

Glu Lys Ala Ala Lys Ile Asn Asp Gly Lys Arg Tyr Val Ser Val Glu
                    740             745             750

Ser Ser Gly Leu His Phe Ile Leu Asp Lys Leu Leu Gly Lys Ile Glu
                    755             760             765

Ser Leu Lys Val Lys Gly Lys Glu Ile Ser Ser Lys Phe Glu Gly Ser
                770             775             780

Ser Ile Thr Phe Trp Arg Pro Pro Thr Asn Asn Asp Glu Pro Arg Asp
    785             790             795             800

Phe Lys Asn Trp Lys Lys Tyr Asn Ile Asp Leu Met Lys Gln Asn Ile
                    805             810             815

His Gly Val Ser Val Glu Lys Gly Ser Asn Gly Ser Leu Ala Val Val
                    820             825             830

Thr Val Asn Ser Arg Ile Ser Pro Val Val Phe Tyr Tyr Gly Phe Glu
                835             840             845

Thr Val Gln Lys Tyr Thr Ile Phe Ala Asn Lys Ile Asn Leu Asn Thr
                850             855             860

Ser Met Lys Leu Thr Gly Glu Tyr Gln Pro Pro Asp Phe Pro Arg Val
    865             870             875             880
```

```
Gly Tyr Glu Phe Trp Leu Gly Asp Ser Tyr Glu Ser Phe Glu Trp Leu
                885                 890                 895

Gly Arg Gly Pro Gly Glu Ser Tyr Pro Asp Lys Lys Glu Ser Gln Arg
            900                 905                 910

Phe Gly Leu Tyr Asp Ser Lys Asp Val Glu Glu Phe Val Tyr Asp Tyr
            915                 920                 925

Pro Gln Glu Asn Gly Asn His Thr Asp Thr His Phe Leu Asn Ile Lys
930                 935                 940

Phe Glu Gly Ala Gly Lys Leu Ser Ile Phe Gln Lys Glu Lys Pro Phe
945                 950                 955                 960

Asn Phe Lys Ile Ser Asp Glu Tyr Gly Val Asp Glu Ala Ala His Ala
                965                 970                 975

Cys Asp Val Lys Arg Tyr Gly Arg His Tyr Leu Arg Leu Asp His Ala
            980                 985                 990

Ile His Gly Val Gly Ser Glu Ala  Cys Gly Pro Ala Val  Leu Asp Gln
            995                  1000                 1005

Tyr Arg  Leu Lys Ala Gln Asp  Phe Asn Phe Glu Phe  Asp Leu Ala
    1010                 1015                 1020

Phe Glu
    1025

<210> SEQ ID NO 7
<211> LENGTH: 46
<212> TYPE: DNA
<213> ORGANISM: Artificial Sequence
<220> FEATURE:
<223> OTHER INFORMATION: LAC12-F

<400> SEQUENCE: 7
tctagagcgg ccgcactagt gccaccatgg cagatcattc gagcag          46

<210> SEQ ID NO 8
<211> LENGTH: 40
<212> TYPE: DNA
<213> ORGANISM: Artificial Sequence
<220> FEATURE:
<223> OTHER INFORMATION: LAC12-R

<400> SEQUENCE: 8
tctagagcgg ccgcgtcgac ttaaacagat tctgcctctg                  40

<210> SEQ ID NO 9
<211> LENGTH: 50
<212> TYPE: DNA
<213> ORGANISM: Artificial Sequence
<220> FEATURE:
<223> OTHER INFORMATION: LAC4-F

<400> SEQUENCE: 9
tctagagcgg ccgcactagt gccaccatgt cttgccttat tcctgagaat        50

<210> SEQ ID NO 10
<211> LENGTH: 44
<212> TYPE: DNA
<213> ORGANISM: Artificial Sequence
<220> FEATURE:
<223> OTHER INFORMATION: LAC4-R

<400> SEQUENCE: 10
tctagagcgg ccgcgtcgac ttattcaaaa gcgagatcaa actc              44
```

<210> SEQ ID NO 11
<211> LENGTH: 43
<212> TYPE: DNA
<213> ORGANISM: Artificial Sequence
<220> FEATURE:
<223> OTHER INFORMATION: gCS8-U

<400> SEQUENCE: 11
tgattcaatc attcttattg gttttagagc tagaaatagc aag                43

<210> SEQ ID NO 12
<211> LENGTH: 43
<212> TYPE: DNA
<213> ORGANISM: Artificial Sequence
<220> FEATURE:
<223> OTHER INFORMATION: gCS8-D

<400> SEQUENCE: 12
caataagaat gattgaatca gatcatttat ctttcactgc gga                43

<210> SEQ ID NO 13
<211> LENGTH: 71
<212> TYPE: DNA
<213> ORGANISM: Artificial Sequence
<220> FEATURE:
<223> OTHER INFORMATION: CS8-IU

<400> SEQUENCE: 13
caaaattacc tacggtaatt agtgaaaggc caaaatctaa tgttacaata aattaaccct    60 cactaaggg a                                                         71

<210> SEQ ID NO 14
<211> LENGTH: 72
<212> TYPE: DNA
<213> ORGANISM: Artificial Sequence
<220> FEATURE:
<223> OTHER INFORMATION: CS8-ID

<400> SEQUENCE: 14
gaccgttccc ttgtgttgta ccagtggtag ggttcttctc ggtagcttct gtaatacgac    60
tcactatagg gc                                                       72

<210> SEQ ID NO 15
<211> LENGTH: 18
<212> TYPE: DNA
<213> ORGANISM: Artificial Sequence
<220> FEATURE:
<223> OTHER INFORMATION: CS8-CKU

<400> SEQUENCE: 15
agtggaacat agaagggg                                                 18

<210> SEQ ID NO 16
<211> LENGTH: 17
<212> TYPE: DNA
<213> ORGANISM: Artificial Sequence
<220> FEATURE:
<223> OTHER INFORMATION: CS8-CKD

<400> SEQUENCE: 16
taagcagccc agtgaac                                                  17

<210> SEQ ID NO 17
<211> LENGTH: 43

-continued

```
<212> TYPE: DNA
<213> ORGANISM: Artificial Sequence
<220> FEATURE:
<223> OTHER INFORMATION: gCS6-U

<400> SEQUENCE: 17
gatacttatc attaagaaaa gttttagagc tagaaatagc aag                43

<210> SEQ ID NO 18
<211> LENGTH: 43
<212> TYPE: DNA
<213> ORGANISM: Artificial Sequence
<220> FEATURE:
<223> OTHER INFORMATION: gCS6-D

<400> SEQUENCE: 18
ttttcttaat gataagtatc gatcatttat ctttcactgc gga                43

<210> SEQ ID NO 19
<211> LENGTH: 60
<212> TYPE: DNA
<213> ORGANISM: Artificial Sequence
<220> FEATURE:
<223> OTHER INFORMATION: CS6-IU

<400> SEQUENCE: 19
aacctcgagg agaagttttt ttacccctct ccacagatcc aggaaacagc tatgaccatg    60

<210> SEQ ID NO 20
<211> LENGTH: 60
<212> TYPE: DNA
<213> ORGANISM: Artificial Sequence
<220> FEATURE:
<223> OTHER INFORMATION: CS6-ID

<400> SEQUENCE: 20
taattaggta gaccgggtag attttttccgt aaccttggtg tctgtaaaac gacggccagt   60

<210> SEQ ID NO 21
<211> LENGTH: 18
<212> TYPE: DNA
<213> ORGANISM: Artificial Sequence
<220> FEATURE:
<223> OTHER INFORMATION: CS6-CKU

<400> SEQUENCE: 21
gtctgccgaa attctgtg                                                 18

<210> SEQ ID NO 22
<211> LENGTH: 18
<212> TYPE: DNA
<213> ORGANISM: Artificial Sequence
<220> FEATURE:
<223> OTHER INFORMATION: CS6-CKD

<400> SEQUENCE: 22
cggtcagaaa gggaaatg                                                 18

<210> SEQ ID NO 23
<211> LENGTH: 33
<212> TYPE: DNA
<213> ORGANISM: Artificial sequences
<220> FEATURE:
<223> OTHER INFORMATION: GRE3-F

<400> SEQUENCE: 23
```

```
catatgtcttt cactggttac tcttaataac ggt                           33
```

<210> SEQ ID NO 24
<211> LENGTH: 35
<212> TYPE: DNA
<213> ORGANISM: Artificial sequence
<220> FEATURE:
<223> OTHER INFORMATION: GRE3-R

<400> SEQUENCE: 24

```
gcggccgcgg caaaagtggg gaatttacca tccaa                          35
```

<210> SEQ ID NO 25
<211> LENGTH: 3547
<212> TYPE: DNA
<213> ORGANISM: Saccharomyces cerevisiae

<400> SEQUENCE: 25

```
tagatcttat acaaaagcaa ctgcgcgctg tggtaaagct acggaaacaa tgtcctatct    60
gtgggaaggt ttgttcgaga ccttcaacac tgaggactca ttacttaata catacgggag   120
acacaccttt caaatgtact tgggagcatt gcaacaaatc tttcaatgtc aagagtaaca   180
tgttaaggca tttaagaacc catcaaaaga aaatagcaaa gaaaaaacat cagtgaaagc   240
attgtttaga atattttgtt ttcagtgtga ttttgatgta ggtgtgacac ttttttaccaa   300
gtaaaatgag tatagatatg tattagttcc atataatata ttacatgtag ccaacaatca   360
attttttactg acttccgatt tttgaatagt gagaggattt tgttcgaat tataatttct   420
acaagaaatt tgtttgcgaa tgcatcagca tttgtaatac ggttctatac tgccgcacga   480
tacatttat tctgtctagt tcgtaagaca aaggaccttt tcatttagta caacgttgcc   540
gacacggatg tcttgatgaa tctctgtacc aggaattcaa ttacctgact agtatgcagt   600
tcactatcaa aaaaaaaaaa aaggttaaat tggtataatc atggttaaag aacaaacagc   660
ctctttcctc tacaaagta tgttaaatgt aggtagttca aattgcggtc acgtatatgc   720
caacgttgtt aatatataat gatccattgg aacaatgaag tttacagaag ctcaaaatta   780
atgcaagaat aattacgtca agggagtcat aacaaactaa gaaaacaaag gaatttgact   840
aagtttgagc gcaatgatat atccatgctt gatattctga ttcatacata tcgtttctgt   900
catttcaatg gaagtcttta tttatcaatt accacaacct ttagtattgt gcttattatt   960
ggtcaaaagg agttcatgcg ctagtgatag tcaacccatg aagtgattag tggaacatag  1020
aagggggataa atttcctatc ggataacaaa gaaaaaccag gattattgtt ttaccaccac  1080
attttcaaac tttcccgctg aatttcctac taccctcatt tgaagaacg ctttccactc  1140
tttaggttgg cgttgtatca tcttttcttc cattcaatgc accagacttt aattttgttg  1200
gttaaactct tattctttgt cagtttaacc aacaaaatta cctacggtaa ttagtgaaag  1260
gccaaaatct aatgttacaa tatgattcaa tcattcttat tgcggagaag ctaccgagaa  1320
gaaccctacc actggtacaa cacaagggaa cggtctcatt gacctcgtgc ataaccggga  1380
aggtaacaca tgaatatgct gtgtttgaat catctccaat ccaaactata ggaatgaaaa  1440
attttttttg ggtacaatgt cttctcacaa tatcgtattc ttggtcagca atgtttccaa  1500
ggatgacaga ctctttctaa gaaaagattt caagttcaaa atttacataa cagtgaacta  1560
tgcagaaaat tttacttcta gaccacgcat ttaacaataa tgtttgcccg caacaataaa  1620
gtatttggtc gctttaagac gttatcagtt attttatgag aaggtgttta ccattcgtgc  1680
tcccatacta aaaccaaggg gtaaatagga cccacatttc gtttctgaca gccaacaacg  1740
```

```
tgccactagc aggacagtta ttggaggttt atattatgta attattgtta gctgataaat    1800
gatttacaga aagcgctgat gttcactggg ctgcttattc agcaatcccc acgcatattt    1860
acttcaaaga gaaagaattt ttgatgtaag ttttatttga acgtggaact ttggcgtggg    1920
gcatttatgg ctgctatcac acaaatcgcg gagcagagta ccctggatt atataacaca    1980 actcactaaa atcgctcaaa attgggggt acgggttagc gcggcagctc atcgagggaa    2040
cagcacctag tgcacgttta attgatagta tcttcagaac gaaatcaaat ttttcgcagt    2100
atcatttacg tttcaagaaa cttaaagtgt ttggagaaat taggaacgaa aaaaagctac    2160
tatagaaatt gtagcctgtc ttcaactgct gtcctcggct tttgacttgc ctaagtatat    2220
gccgcaatgg gcgataagcg ggagtgtcgg tcagatctgt ggtaaaaaaa agatagcaat    2280
aaaaaattat gaatttaaac agtagtcttg aatttaaaca agtgatcttg acttgaatac    2340
ttccatcaat gagtcgctaa aatgaaaatg gctgcacaat ctcctccgca tatcttaaaa    2400
ggcagcaatt agccagttga tcaccctaca tttccacaga aacgaaaaag tgtaatagtt    2460
atttttgcgg ccaatatcgt aagctctagc ggtgccttag ctttatgatt gttgcaagaa    2520
agtttgcctt tttgactctc cttcaggtgt cagtattaac aaacggcgtt gaatgtttaa    2580
gttattattt tattcatcaa atcgacttgg atactttctc ggtgatgtcg ctaattggat    2640
tataccatta aggttgtcac cagtgtaaaa attttgcatc ggtacttgca actacgtgtg    2700
aaggtcaagt tactcaacgc aaagaaacgt taacattttt acaaatttta gctgcagtac    2760
tatgttttaa gtaatccaaa gggaactatt tgttatatcc cagaattatt tacattcgtt    2820
tcttagtttc ataaacaatg aatacctatt gaatggatag aaattctgac ttgatttttac    2880 gagttattat tgctgacatt agtccaaaga catctcagtt ttgtttcctc tacaacccaa    2940
tgaggaggct agccagggct gtcgcccaaa aaaatagcca ataaagcggc aactttctgt    3000
atgtcttgca ttttttccgc tgacttggga gtagagtaca gctgcgcgga gtcgcgtatt    3060
acaaatcttg tactttgcat tctgtgcata cgtgaggaaa aagcagcacc tgttgtgaaa    3120
aaagataaat ttcttttttt cattttcta tcctcaaagg aaaatctttt ctgcgaaatt    3180
tctagccgct cttcagtttc cgaagtaaag tcgctgaggc cgaaaacaa ctttatttgc    3240 ccacacgctg ttataggctt ccagggagca aaagcgcaat tgggaataag gtttcctcaa    3300
ttgaatggtt tgcttcgcct acagcattaa ccagaaggta atttgatctc ttgtatgtcc    3360
gctaacagat cttgtccatt aattgtttat tttcttcagg taggctgagc ccactttgta    3420
gtagctccct accattactt ttggccttgt agttattggc tttgattttt tctttctatg    3480
acaatcccgt tgagcaacct tgcgaagggc tcttttttgaa aaaaggcgt gggcaagatc    3540 tctgtat                                                              3547
```

<210> SEQ ID NO 26
<211> LENGTH: 1969
<212> TYPE: DNA
<213> ORGANISM: Saccharomyces cerevisiae

<400> SEQUENCE: 26

```
ataaaatgaa acggacagga attgaacctg caacccttcg attgcaatct tattccgtgg     60
aatttccaag atttaattgg agtcgaaagc tctaccattg agccaccgct tcatcttgaa    120
atatcgaaga tataacattt tacttgtctg ccgaaattct gtgtttgcta taatgtttga    180
attagaatct cttaaaatag ctactcatac ttcttcataa ctaatccatt agtgaccata    240
```

```
                                                       -continued
tgaagtaatc ggacgccaca catcattgat gtttcacgat ggagaatgat aacacactaa    300
gtggcattgt gggcaaagta agttaaacac ctattgctca aatgatcaac ttggtgtttg    360
cacatatacg gatgtaagtc atgacattga aatcataata tgctttcatg ataatcatat    420
gagcatgttt aatattacta ataaggctgt attctatact tctcttatat agaataagaa    480
gatctgcatt tattcttgat tgacactaca gttcaacaat taattaccaa cagaattaat    540
tactacctat cgttcacaag ctactacgtt atcatacaca atgtaaaaat atgacacaaa    600
aatggaaaac cgtcatcaga tttaatgggg ctgaaacaca agaattcata atgtgataga    660
ataatgggtg aagtgtataa agaagaatat ataatattac tgtgtagaaa tatcaatttc    720
cctttgtgag ttctcataac ctcgaggaga agttttttta cccctctcca cagatcgata    780
cttatcatta agaaaatggg acaccaaggt tacgaaaaa tctacccggt ctacctaatt     840
actctcttgg cgcactagtt ttccgaaaaa aacaggtaaa ttcttcttta gataaagata   900
aatataaaac ttcacagcca ttcactcaca caaactagtc ccttagggtg cgtataatga   960
tctgtacatc ttatttctat atatcttacc gtgtatttt  tcttttctca attcttgttc  1020
gcaaataaaa agatattcgt gtttgtggaa gaacactagt tccgttttgt attcaacctg  1080
gaaatttaca atagatcttc atcatcgtat gtctaccatg ttaatctccc gttaaactgt  1140
ttcacgttat caagattatg tcatctattc ctgggcgaac ataattcctt acaaaaacat  1200
ttgtcattac acaagtgtaa gggtaatga  aaagtaattt tgttacaagt acgcaaaatt  1260
cgtttatttc aagaaacact aaggatcgtc atttcccttt ctgaccgatg ttccttcttt  1320
ttgctatttt tttcccgagt catctcatcg ttttgagttt ttcctagtcc attaaattgt  1380
caccttactc tcggaaaaaa gaaacgacaa atgctcctag tgccgttttt cgaagcttga  1440
aaaaaaaaat tgcaaattat ttaattttgc tgctaaggag ttgaagtagg tgcattccgc  1500
cttattgatc accctgttag atttgttgcg atcgttatag tgctagtttg tccattgttg  1560
tgtcataaaa gatagctttg ggagaaaatt catcaaaaca acatatcatc agcgttatta  1620
caattcattg tccttcccaa gttttttga  cgtataatat tatcgctatc tgactcatta  1680
gtacacaaat acagatatac aacctcaaaa tcaaaaatgc ctagaaaccc attgaaaaag  1740
gaatattggg cagatgtagt tgacggattc aagccggcta cttctccagc cttcgagaat  1800 gaaaagaat  ctactacatt tgttaccgaa ctaacttcca aaaccgattc tgcatttcca  1860
ttaagtagca aggattcacc tggcataaac caaaccacaa acgatattac ctcttcagat  1920
cgcttccgtc gtaatgaaga cacagagcag gaagacatca acaacacca              1969
```

METHOD FOR BIOLOGICALLY PRODUCING SUGAR ALCOHOL FROM AGAR

CROSS REFERENCE TO RELATED APPLICATIONS

This application is a National Stage of International Application No. PCT/KR2019/011505 filed Sep. 5, 2019, claiming priority based on Korean Patent Application No. 10-2018-0106567 filed Sep. 6, 2018.

INCORPORATION BY REFERENCE OF SEQUENCE LISTING

The content of the electronically submitted sequence listing, file name: Q261923_substitute sequence listing as filed; size: 35,837 bytes; and date of creation: May 14, 2024, filed herewith, is incorporated herein by reference in its entirety.

TECHNICAL FIELD

The present invention relates to a method of biologically producing novel sugar alcohols, 3,6-anhydro-L-galactitol (L-AHGol) and agarobititol (ABol) which is a disaccharide having the L-AHGol as a reducing end, from marine algae using GRAS strains.

BACKGROUND ART

The ocean accounts for about 71% of the earth and has an environment very different from land, such as low temperature, high pressure, a small amount of light, low oxygen content, and high salt content. Marine organisms living in this environment are very diverse and also have unique characteristics different from those of terrestrial organisms. Among marine organisms, marine algae are composed of unique components unlike land plants. In particular, marine algae have very unique characteristics such as absorbing and preserving moisture well due to carbohydrates that are not found in land plants.

Among marine algae, especially, agar, which is obtained from red algae, retains moisture to form a gel, and therefore, it has been widely used in the food and pharmaceutical industry. Agarose, which is a major polysaccharide constituting the agar, is a polymer consisting of 3,6-anhydro-L-galactose (L-AHG) and D-galactose (D-Gal) alternately linked by an α-1,3-bond and a β-1,4-bond. In this case, L-AHG, which is a rare sugar that does not exist in terrestrial organisms, can be used as a cosmetic material due to having excellent whitening and moisturizing effects and is a multifunctional high value-added material with anti-inflammatory, anti-caries, and colon cancer prevention effects. Due to the functionality of L-AHG, many studies have been conducted to produce L-AHG from red algae for use as a high value-added material. In addition, agarobiose (AB) which is a disaccharide having L-AHG as a reducing end is known to have an excellent anti-inflammatory effect.

However, although L-AHG and AB are high value-added materials with multifunctionality, it is difficult to industrially use L-AHG and AB. This is because L-AHG and AB are very unstable under conditions of high temperatures and acids and thus are easily converted into 5-hydroxymethyl furfural (5-HMF) and the like and lose the functionality thereof.

Therefore, to solve the problem of the thermal stability of not only L-AHG but also AB, it is intended to convert the sugars into the corresponding novel sugar alcohols. Sugar alcohols generally refer to all types of sugars whose aldehyde group or ketone group is substituted with an alcohol group by adding hydrogen. Sugar alcohols have a variety of functions that natural sugars do not have and also have lower sweetness than natural sugars and a refreshing feeling. For this reason, various sugar alcohols such as sorbitol, xylitol, mannitol, and the like have been used as food additives, and maltitol, lactitol, erythritol, and the like are themselves treated as foods. In addition, sugar alcohols may be converted into useful chemicals through chemical and biological catalytic reactions. In this way, sugar alcohols are potential high value-added materials, and there is a need for production of novel sugar alcohols.

There have been no reports about production of sugar alcohols, agarobititol (ABol) and 3,6-anhydro-L-galactitol (L-AHGol), from agar or agarose of red algae in yeast which is a eukaryotic cell.

The inventors of the present invention established optimal conditions for producing ABol and L-AHGol by introducing enzyme genes derived from *Kluyveromyces lactis* (NRRL: Y-8279) into yeast and produced a high concentration and high yield of sugar alcohols for the first time by culturing the yeast, thereby completing the present invention.

RELATED-ART DOCUMENTS

Korean Unexamined Patent Publication No. 10-2017-0114785

DISCLOSURE

Technical Problem

The present invention is directed to providing recombinant yeast and a method of mass-producing agarobititol (ABol) and 3,6-anhydro-L-galactitol (L-AHGol) using the recombinant yeast, which are intended to produce sugar alcohols, ABol and L-AHGol, from the yeast using an enzymatic recombination technique.

Technical Solution

Yeast is known to have higher resistance to ethanol, organic acids, and inhibitors than other bacteria and also known as a safe microorganism widely used in foods such as bread and wine. Therefore, yeast has been widely used in the production of biofuels and chemical materials.

3,6-anhydro-L-galactose (L-AHG) is a high value-added material with multifunctionality, but L-AHG is greatly affected by temperature and thus easily converted into 5-HMF. To solve this problem, it is intended to produce 3,6-anhydro-L-galactitol (L-AHGol) which is a sugar alcohol of L-AHG. To produce L-AHGol, two major conditions are required. First, agarobiose (AB) or L-AHG needs to be efficiently, easily, and simply produced from red algae. Second, the AB and L-AHG thus produced need to be converted into agarobititol (ABol) and L-AHGol, respectively.

First, various studies have been conducted to produce L-AHG and AB. As representative methods, first, there is a method of hydrolyzing agar or agarose using an acid at high temperatures to produce AB and L-AHG. Second, there is a method of hydrolyzing agar or agarose using endo- and exo-β-agarases to produce neoagarobiose (NAB) and then producing L-AHG using α-neoagarobiose hydrolase (α-NABH). Third, as a combination of the first and second methods, there is a method of liquefying agar or agarose using a chemical catalyst and then using the β-agarases and α-NABH. Recently, a process of not only liquefying a high concentration of agarose using phosphoric acid as a catalyst but also selectively hydrolyzing only an α-1,3-glycosidic bond to produce L-AHG and AB at one time has been studied. Since the AB thus produced may be hydrolyzed using only one type of enzyme, which enables the hydrolysis of AB, to produce L-AHG and D-Gal which are monosaccharides, this process may be very simple and efficient.

Subsequently, to convert the produced AB and L-AHG into ABol and L-AHGol, which are sugar alcohols thereof, the AB and L-AHG need to be reduced. As methods therefor, there are a chemical method using a chemical reductant and a biological method using a reductase. With the development of genetic engineering technology today, research has been conducted on the production of xylitol, which is a representative sugar alcohol, by a biological method using *Saccharomyces cerevisiae* yeast into which a reductase that allows xylose to be reduced to produce xylitol is introduced.

Therefore, to efficiently produce novel sugar alcohols, ABol and L-AHGol, from agar or agarose of red algae, the present invention is intended to combine, through a metabolic engineering method, a process of producing agarobiose (AB) from agarose using phosphoric acid and then producing L-AHG using an enzyme that allows the AB to be hydrolyzed and a process of conversion into ABol and L-AHGol by a biological reduction reaction by which the L-AHG is reduced using an enzyme.

Therefore, the present invention provides recombinant yeast for producing a sugar alcohol using agarobiose as a substrate, which includes a gene encoding aldose reductase (AR) and a gene encoding lactose permease.

The recombinant yeast may further include a gene encoding β-galactosidase. One or more of the gene encoding aldose reductase, the gene encoding lactose permease, and the gene encoding β-galactosidase may be foreign genes derived from other yeast species or inherent genes of the recombinant yeast.

According to a specific embodiment, *Saccharomyces cerevisiae* yeast does not absorb agarobiose so that the agarobiose is used as a substrate, and does not include an enzyme that allows agarobiose to be hydrolyzed into a monosaccharide. Accordingly, the inventors of the present invention have attempted to introduce a LAC12 gene encoding lactose permease which is a lactose transporter so that the yeast is able to absorb agarobiose into the cell and further introduce a LAC4 gene encoding β-galactosidase which is an enzyme that allows agarobiose to be saccharified to produce L-AHG.

More specifically, the gene encoding aldose reductase may be an inherent gene of the recombinant yeast, and the gene encoding lactose permease and/or the gene encoding β-galactosidase may be a foreign gene(s).

Even more specifically, the recombinant yeast of the present invention is *Saccharomyces cerevisiae* in which an inherent GRE3 gene represented by SEQ ID NO: 1 is a gene encoding aldose reductase, and a LAC12 gene represented by SEQ ID NO: 2, which encodes lactose permease which is a lactose transporter, and/or a LAC4 gene represented by SEQ ID NO: 3, which encodes β-galactosidase which is an enzyme that allows agarobiose to be hydrolyzed (saccharified) to produce L-AHG, are/is transformed as a foreign gene(s) into the yeast. The gene encoding lactose permease and the gene encoding β-galactosidase are derived from *Kluyveromyces lactis* (NRRL: Y-8279).

Therefore, the recombinant yeast for producing a sugar alcohol produced from agar or agarose of red algae, which includes the enzymes, allows the agarobiose to be converted into agarobititol which is a reduced form thereof and also allows the agarobiose to be hydrolyzed to produce L-AHG which is a monosaccharide and then the L-AHG to be converted into L-AHGol which is a reduced form of L-AHG.

Specifically, agarobiose absorbed into the recombinant yeast is used as a starting material, the agarobiose is subjected to a two-step enzymatic reaction in the cell to produce sugar alcohols, and this reaction is as shown in FIG. 1. More specifically, agarobiose, which is a substrate, may be hydrolyzed by β-galactosidase to produce L-AHG and D-galactose which are monosaccharides, and the L-AHG may be converted into L-AHGol, which is a sugar alcohol, by aldose reductase. In addition, the aldose reductase may allow agarobiose, which is an initial substrate, to be converted into ABol which is a sugar alcohol. Therefore, the sugar alcohols produced by the recombinant yeast may be L-AHGol and ABol.

The aldose reductase may be presented by an amino acid sequence set forth in SEQ ID NO: 4, and the lactose permease and β-galactosidase may be presented by amino acid sequences set forth in SEQ ID NOS: 5 and 6, respectively.

The above-described genes include polynucleotides encoding proteins having the physicochemical activity of the enzymes and including one or more deleted, substituted, inserted, and/or added amino acids. For example, the genes include any one polynucleotide set forth in SEQ ID NOS: 1 to 3 and also include polynucleotides encoding proteins having the physicochemical properties of the enzymes, which has been hybridized under strict conditions. The "polynucleotide hybridized under strict conditions" refers to a polynucleotide hybridized, for example, to one or more probe DNAs including a sequence of at least 20, and preferably, at least 30 consecutive residues (e.g., 40, 60, or 100 consecutive residues) optionally selected from enzyme proteins under conditions described in the instructions (washing with a 0.5×SSC-containing primary washing buffer at 42° C.) using a ECL direct nucleic acid labeling/detection system (Amersham Pharmacia Biotech). In the present invention, a "polynucleotide" includes an isolated polynucleotide. The "isolated polynucleotide" refers to a polynucleotide that exists in a form different from a naturally occurring polynucleotide. For example, a vector and polynucleotide integrated into the genome of another organism are included in the isolated polynucleotide. In addition, the isolated polynucleotide includes a polynucleotide obtained as cDNA, a PCR product, or a restriction fragment. Additionally, a polynucleotide used as a part of a polynucleotide encoding a fusion protein is also included in the "isolated polynucleotide".

Polynucleotides encoding the above-described enzymes of the present invention may be isolated, for example, by a method described below. PCR primers are designed based on polynucleotide sequences set forth in SEQ ID NOS: 1 to 3, respectively, and PCR is performed using chromosomal DNA derived from an enzyme-producing strain as a template or a cDNA library to obtain DNA of the present invention.

In addition, the polynucleotides of the present invention may be prepared using a DNA fragment obtained as a probe through colony hybridization, plaque hybridization, or the like, specifically, by screening (a) a library obtained by introducing a restriction enzyme fragment of chromosomal DNA derived from an enzyme-producing strain into a phage or plasmid and transforming the phage or vector into *E. coli* cells or (b) a cDNA library.

Alternatively, the polynucleotides of the present invention may be obtained by analyzing the nucleotide sequence of a DNA fragment obtained by PCR; designing a PCR primer based on the analyzed sequence to extend a strand outside of a known DNA sequence; and digesting chromosomal DNA derived from an enzyme-producing strain with an appropriate restriction enzyme and performing reverse-PCR by a self-cyclization reaction using the DNA as a template (Genetics, 120, 621-623 (1988)). In addition, the polynucleotides of the present invention may be obtained by RACE (Rapid Amplification of cDNA End; 'PCR Jikken Manual (Manual for PCR Experiments)', 25-33, HBJ Publishing Bureau).

In addition to the genomic DNA and cDNA cloned by the above method, the polynucleotides of the present invention include synthesized DNAs.

In the present invention, a "recombinant vector" is a vector capable of expressing a protein of interest in a suitable host cell and refers to a gene construct including essential regulatory elements operably linked to express a gene insert.

The vector includes a plasmid vector, a cosmid vector, a bacteriophage vector, a viral vector, or the like, but the present invention is not limited thereto. A suitable expression vector includes, in addition to expression control elements such as a promoter, an operator, an initiation codon, a termination codon, a polyadenylation signal, and an enhancer, a signal sequence or a leader sequence for membrane targeting or secretion, and may be prepared in various forms according to purpose. The promoter of the vector may be constitutive or inducible. In addition, the expression vector includes a selection marker for selecting a host cell containing the vector, and a replicable expression vector includes the origin of replication.

The recombinant vector of the present invention may be preferably prepared by inserting each or all of the above-described enzyme-encoding nucleic acids into a general vector for expression of a *E. coli* strain. As the vector for expression of an *E. coli* strain, any vector for expression of an *E. coli* strain, which is generally usable, may be used without limitation.

According to a specific embodiment, the method of the present invention uses a CRISPR/Cas9 system for transforming foreign genes into yeast and for more stably expressing the genes. Donor plasmids containing the genes encoding the enzymes and guide plasmids for introducing the genes by cleavage at a specific location were prepared and introduced into host cells together with CRISPR/Cas9 to produce recombinant yeast.

The transformation may be performed by any method of introducing a nucleic acid into an organism, cell, tissue, or organ and, as known in the art, by selecting an appropriate standard technique according to a host cell. The method includes electroporation, protoplast fusion, calcium phosphate ($CaPO_4$) precipitation, calcium chloride ($CaCl_2$)) precipitation, agitation using silicon carbide fibers, agrobacteria-mediated transformation, PEG, dextran sulfate, Lipofectamine, and the like, but the present invention is not limited thereto.

The recombinant yeast may be one or more of *Saccharomyces cerevisiae, Pichia pastoris, Schizosaccharomyces, Kluyveromyces lactis, Neurospora crassa, Yarrowia lipolytica, Pichia angusta, Candida boidinii*, and *Blastobotrys adeninivorans*, but the present invention is not limited thereto. According to a specific embodiment, *Saccharomyces cerevisiae* is used as the recombinant yeast.

The present invention also provides a method of producing a sugar alcohol, which includes fermenting the above-described recombinant yeast for producing a sugar alcohol using a substrate and a carbon source.

In general, transformed cells (including yeast) may not absorb a substrate that was not used prior to transformation or have no resistance to a product newly produced from the substrate. Therefore, the substrate or product may interfere with the metabolism of the transformed cells or act as a toxic substance, which is one cause of inhibition of the production of a desired product. According to an embodiment of the present invention, as a result of confirming the sugar alcohol production efficiency of the recombinant yeast of the present invention and the cytotoxicity of a substrate, it was confirmed that agarobiose, which is a substrate, interferes with the metabolism of the transformed strain and thus inhibits the growth thereof. Accordingly, the inventors of the present invention have found a new method for mass production of a sugar alcohol.

Accordingly, the present invention provides a method of mass-producing a sugar alcohol, which includes: subjecting the recombinant yeast to high cell-density culture; producing a high concentration of agarobiose as a substrate; and subjecting the high cell-density cultured recombinant yeast to fed-batch culture using the produced high concentration of agarobiose and one or more of D-Gal, D-Glc, and lactose as a carbon source to induce fermentation.

According to a specific embodiment, as the concentration of agarobiose, which is a substrate, increases, the recombinant yeast absorbs less carbon sources, and thus cell growth is inhibited. For this reason, for mass production of a sugar alcohol, which is a final product, a high concentration of agarobiose and high cell-density cultured recombinant yeast are reacted, and thus the growth inhibition problem may be solved.

The concentration of the high cell-density cultured recombinant yeast may specifically range from 4 g/L to 90 g/L, and more specifically, from 5 g/L to 40 g/L. The concentration of agarobiose, which is a substrate, may range from 100 g/L to 300 g/L, and specifically, from 100 g/L to 150 g/L.

In addition, to increase the growth rate of the recombinant yeast, a carbon source or substrate is constantly supplied to a medium through fed-batch culture (fed-batch fermentation), and the supply amount of the carbon source or substrate and the usage amount of cells are equalized to prevent the absorption of the substrate or carbon source from being inhibited. Also, to minimize the production of galactitol (Galol) which is a by-product, D-Gal may be used as a carbon source.

More specifically, the fed-batch culture of the recombinant yeast may be performed 3 to 7 times using D-Gal as a carbon source to induce the sufficient growth of cells and then additionally performed 3 to 7 times using agarobiose as a substrate to obtain a desired sugar alcohol with high yield.

Descriptions of the recombinant yeast and the enzymatic reaction described in the method of the present invention are the same as described above and therefore will be omitted to avoid repetition.

Advantageous Effects

According to the present invention, recombinant yeast capable of biosynthesizing a sugar alcohol is produced and subjected to a combination of high cell-density culture and fed-batch culture, and thus agarobititol and 3,6-anhydro-L-galactitol (L-AHGol) can be mass-produced.

DESCRIPTION OF DRAWINGS

FIG. 1 is a schematic diagram of the production of L-AHGol from red algae by a biological method using *S. cerevisiae*.

FIG. 2 shows an SDS-PAGE result obtained after cloning of a GRE3 gene derived from *S. cerevisiae* into a pET21α+ vector, overexpression using *Escherichia coli*, and purification.

FIGS. 3A-3J show results of the reactivity of L-AHG and AB with AR overexpressed by *S. cerevisiae*-derived GRE3. FIG. 3A shows a structural change by conversion of L-AHG and AB into L-AHGol and ABol by reaction with AR and the molecular weight thereof. FIG. 3B shows a result of the reactivity of L-AHG and AB when reacted with AR, as obtained by measuring a tendency in which NADPH, which is a cofactor, decreases at 340 nm using a spectrophotometer. In this case, xylose and galactose are used as positive controls. FIG. 3C shows a total ion chromatography (TIC) result obtained by measuring products before and after the reaction of L-AHG with AR through gas chromatography-mass spectrometry (GC/MS). FIG. 3D shows a characteristic mass spectrum of L-AHG in a product before the reaction of L-AHG with AR. FIG. 3E shows a characteristic mass spectrum of produced L-AHGol in a product after the reaction of L-AHG with AR. FIG. 3F shows a mass spectrum of produced L-AHGol in a product after the reaction L-AHG of with AR, as obtained by LC/MS-IT-TOF analysis. FIG. 3G shows a TIC result obtained by measuring products before and after the reaction of AB with AR through GC/MS. FIG. 3H shows a characteristic mass spectrum of AB in a product before the reaction of AB with AR. FIG. 3I shows a characteristic mass spectrum of produced ABol in a product after the reaction of AB with AR. FIG. 3J shows a tandem mass spectrum of produced ABol in a product after the reaction of AB with AR, as obtained by LC/MS-IT-TOF analysis, and an inserted diagram of FIG. 3J shows a mass spectrum of ABol.

FIGS. 4A-4F show experimental results of confirming an effect of bringing AB into the cell in a minimal medium for genetically engineered D452-2-L12, into which a *K. lactis*-derived LAC12 gene capable of expressing a lactose transporter is introduced, and a parent strain D452-2. FIG. 4A shows a result of consuming AB with D452-2-L12 without a carbon source, FIG. 4B shows a result of consuming AB with D452-2-L12 when glucose is provided as a carbon source, FIG. 4C shows a result of consuming AB with D452-2-L12 when galactose is provided as a carbon source, FIG. 4D shows a result of consuming AB with a parent strain D452-2 without a carbon source, FIG. 4E shows a result of consuming AB with a parent strain D452-2 when glucose is provided as a carbon source, and FIG. 4F shows a result of consuming AB with a parent strain D452-2 when galactose is provided as a carbon source.

FIG. 5 shows a result of a coenzyme experiment for examining the AB hydrolysis effect of genetically engineered D452-2-L124 into which a *K. lactis*-derived LAC4 gene capable of expressing β-galactosidase is introduced and strains into which LAC4 is not introduced. As experimental strains, D452-2-L124, D452-2-L12, and parent D452-2 were used and compared, and an inserted diagram of FIG. shows a result of a coenzyme experiment of the strains with respect to lactose as a positive control.

FIGS. 6A-6B show experimental results of confirming an inhibition effect of AB on cell growth and glucose (carbon source) consumption of D452-2, D452-2-L12, and D452-2-L124 in a minimal medium. FIG. 6A shows a result of the specific growth rate of the strains according to an AB concentration, and FIG. 6B shows a result of the glucose consumption rate of the strains according to an AB concentration.

FIGS. 7A-7D show the fermentation tendency of a high concentration of a D452-2-L124 strain to produce L-AHGol in a minimal medium according to an AB concentration. FIGS. 7A to 7D show the fermentation tendency of the D452-2-L124 strain when 10 g/L of AB, 20 g/L of AB, 45 g/L of AB, and 90 g/L of AB were used as substrates, respectively.

FIG. 8 shows a high-performance liquid chromatography (HPLC) result of AB produced by hydrolyzing 20% (w/w) agarose with phosphoric acid.

FIG. 9 shows the fermentation tendency of D452-2-L124 to produce L-AHGol through AB fed-batch culture in a fermentor using a minimal medium.

FIG. 10 a result of separation and purification of L-AHGol produced using a fermentor in FIG. 9 by size exclusion chromatography using a G-10 resin.

FIGS. 11A-11D show experimental results of confirming the thermal stability of L-AHG and AB and the corresponding sugar alcohols, L-AHGol and ABol. FIG. 11A to 11D show results of the thermal stability of L-AHG, AB, L-AHGol, and ABol, respectively.

MODES OF THE INVENTION

Hereinafter, the present invention will be described in more detail with reference to examples according to the present invention. However, it should be understood that the following examples are given for the purpose of illustration only and are not intended to limit the scope of the present invention.

<Example 1> Cloning of *S. cerevisiae*-Derived GRE3 Gene Expressing AR, Overexpression Using *E. coli* (DE3), and Purification To obtain the genomic DNA of *S. cerevisiae* D452-2, D452-2 was cultured in a 20 g/L glucose-containing YP medium at 30° C. for 24 hours. Genomic DNA was extracted using a commercial DNA extraction kit (Qiagen, Valencia, CA, USA). A target gene GRE3 was amplified from the genomic DNA by PCR. The primers used herein were 5'-CATATGTCTTCACTGGTTACTCTTAATAACGGT-3' (forward; SEQ ID NO: 23) and 5'-GCGGCCGCGGCAAAAGTGGGGAATTTACCATC-CAA-3' (reverse; SEQ ID NO: 24). To easily purify the protein using affinity chromatography, the base sequence of a gene encoding 6 histidines at the C-terminus was added. The PCR product and pET21a vector were cleaved with NdeI and NotI, respectively, and ligated to construct a pET21a_AR plasmid. The plasmid was transformed into *E. coli* Top10.

To overexpress the gene thus obtained, the gene was transformed into a host for protein expression, *E. coli* BL21 (DE3). The cells were cultured in a Luria-Bertani (LB) medium containing 50 mg/L of ampicillin at 37° C. until the absorbance at 600 nm reached 0.4 to 0.6. 0.1 mM IPTG was added to induce the expression of the protein, the induction temperature was set to 16° C., and the protein was overexpressed in a water-soluble form for 16 hours. After the cultivation was completed, the cells were recovered by centrifugation, released with a 20 mM Tris-HCl buffer (pH 7.4), and then lyzed using a sonicator. The resultant was centrifuged again at 10,000 g to obtain a supernatant. The recombinant protein was purified using a HisTrap column (GE Healthcare, Piscataway, USA). The purified protein was concentrated with an Amicon Ultra centrifugal filter (30,000 molecular weight cutoff; Millipore, Billerica, MA, USA), and the concentration of the protein was measured using a bicinchoninic acid (BCA) protein assay kit (Thermo Fisher Scientific, San Hose, CA, USA).

As an 8% SDS-PAGE result for AR thus expressed, 37.1 kDa was confirmed (FIG. 2).

<Example 2> Measurement of Reduction of L-AHG and AB by AR

Until now, there have been no research results confirming whether it is possible to biologically convert a substrate L-AHG into the corresponding sugar alcohol, L-AHGol, using enzymes. In this study, to convert L-AHG into L-AHGol, an inherent enzyme AR expressed by a GRE3 gene derived from *S. cerevisiae*, which is a GRAS strain, was examined. *S. cerevisiae*-derived AR is known to react extensively with various aldoses having aldehyde groups, such as glucose, xylose, arabinose, and glyceraldehyde, to produce the corresponding sugar alcohols.

To confirm AR reactivity, not only L-AHG and AB but also xylose and galactose as positive controls were used as substrates. An enzymatic reaction was performed in a pH 6.0 sodium phosphate buffer at 30° C. 1 mM NADPH was used as a cofactor, and each substrate was allowed to react at 2 mM and a protein concentration of 9.36 nmol. FIGS. 3A-3J show results of the AR enzyme reaction. As shown in FIG. 3A, when L-AHG and AB were converted into L-AHGol and ABol by reduction with AR, hydrogen was added to an aldehyde group, and thus a structural change occurred. Accordingly, the molecular weight thereof was also changed from 162 (L-AHG) to 164 (L-AHGol) and from 324 (AB) to 326 (ABol). As shown in FIG. 3B, AR reacted best with xylose which is a positive control and then with L-AHG. In this case, interestingly, AB, which is a disaccharide having L-AHG as a reducing end, was also converted into ABol by AR.

To confirm that L-AHG and AB were actually converted into L-AHGol and ABol by AR, products before and after the enzymatic reaction were measured using GC/MS and LC/MS-IT-TOF. First, a derivatization process for GC/MS analysis was as follows. 20 µl of products before and after the AR enzyme reaction of L-AHG and AB were dried using a speed vac. For derivatization, 10 µl of 4% (w/v) o-methylhydroxylamine hydrochloride in pyridine was added to the dried samples and allowed to react at 30° C. for 90 minutes. Afterward, 45 µl of N-methyl-N-(trimethylsilyl)trifluoroacetamide was added and allowed to react at 37° C. for 30 minutes. In this case, an Agilent 7890A GC/5975C MSD system equipped with an RTX-5Sil MS (30 m×0.25 mm i.d., 25 µm film thickness, Restek) column was used for analysis. The temperature of the column was first maintained at 150° C. for a minute, raised to 330° C. at 20° C./min, and then maintained for 5 minutes. 1 µl of the samples were analyzed in a splitless manner. A total ion chromatography (TIC) result of FIG. 3C showed the peak of L-AHG in the product after the enzymatic reaction was reduced compared to the peak of L-AHG before the enzymatic reaction, and a peak presumed to be L-AHGol, which was not present in the product before the enzymatic reaction, appeared. FIGS. 3D and 3E show mass spectra of L-AHG and L-AHGol, respectively.

To confirm produced L-AHGol in the product after the AR enzyme reaction, analysis was performed by liquid chromatography hybrid ion trap time-of-flight mass spectrometry (LC/MS-IT-TOF). Conditions for LC/MS-IT-TOF analysis are as follows. As a column, a Hypercarb porous graphitic carbon LC column (100×2.1 mm, packed with 3 µm particles) was used, and the temperature of the column was maintained at 70° C. during analysis. A mobile phase consisted of 25 µM lithium chloride and acetonitrile and had a gradient of 0 to 80% during analysis at a flow rate of 0.2 mL/min for 41 minutes. Electrospray ionization was performed in a positive ion mode, and source-dependent parameters were set as follows: nebulizing gas flow: 1.5 L/min, interface voltage: 4.5 kV, detector voltage: 1.65 kV, curved desolvation line (CDL), and heat block temperature: 200° C. Mass spectrometry was performed in a range of 100 to 700 m/z. When L-AHG was converted into L-AHGol, the molecular weight of L-AHGol was 164. In this case, a lithium ion was added to L-AHGol, and thus the actually measured molecular weight was 171 (FIG. 3F).

In addition, a GC/MS analysis result showed that AB was converted into ABol by AR. The peak of AB before the enzymatic reaction was reduced after the enzymatic reaction, and a new peak presumed to be ABol appeared (FIG. 3G). FIGS. 3H and 3I show mass spectra of AB and ABol, respectively. Also, an LC/MS-IT-TOF analysis result showed, when AB was converted into ABol, the molecular weight of ABol was 326. In this case, a lithium ion was added to ABol, and thus the actually measured molecular weight was 333. As shown in FIG. 3J, the product produced after the enzymatic reaction had a molecular weight of 333, and as a result of confirming the chemical structure of the product by the tandem mass spectrum of ABol, it can be seen that peaks at 171.1330 which is a molecular weight of L-AHGol having a lithium ion added thereto and 169.1192 which is a molecular weight of galactose excluding a water molecule and having a lithium ion added thereto were exhibited, indicating that L-AHG present at a reducing end of ABol was converted into L-AHGol by AR, and thus L-AHGol and galactose were included.

<Example 3> Preparation of Strain Capable of Producing L-AHGol from AB

D452-2-L124 that is able to consume AB was prepared as follows. LAC12 was cloned into a pRS423-pGPD plasmid. A LAC12 gene fraction was amplified from genomic DNA of *K. lactis* (NRRL: Y-8279) by PCR using LAC12-F and LAC12-R primers (Table 3). The PCR product and pRS423-GPD plasmid were cleaved with restriction enzymes SpeI and SalI, respectively, and then ligated to construct pRS423-pGPD-LAC12. A LAC4 gene was also constructed from *K. lactis*. LAC4 was amplified by PCR using LAC4-F and LAC4-R primers (Table 3), cleavage with restriction enzymes SpeI and SalI was performed like the pRS425-pGPD plasmid, and then ligation was performed to construct pRS425-pGPD-LAC4.

To introduce genes into the genome of a parent strain D452-2 using CRISPR/Cas9 for stably expressing the genes, guide plasmids p42K-CS8 and p42K-CS6 were made as shown in Table 3. To construct p42K-CS8 and p42K-CS6, a pRS42K plasmid was subjected to reverse PCR using a pair of gCS8-U and gCS8-D primers and a pair of gCS6-U and gCS6-D primers, which included a guide RNA base sequence (Table 3). The 20 bp target base sequence of the guide RNA was bound to the empty locus of chromosome XVI (CS8) and VII (CS6) (Tables 4 and 5). Then, the target genes of interest were introduced into the chromosomal position by homologue recombination without affecting the function of other genes.

To introduce LAC12 into the genome of the D452-2 strain based on CRISPR/Cas9, as donor DNA, the pRS423-pGPD-LAC12 plasmid was amplified using CS8-IU and CS8-ID primers. CS8-LAC12-introduced cells were confirmed by PCR using CS8-CKU and CS8-CKD primers. The strain thus prepared was D452-2-L12 (Table 1). Similarly, in the case of CS6-LAC4, donor DNA amplified from the pR425-pGPD-LAC4 plasmid using CS6-IU and CS6-ID primers was introduced into D452-2-L12. CS6-LAC4-introduced cells were confirmed using CS6-CKU and CS6-CKD primers, and the strain thus prepared was D452-2-L124 (Table 1).

TABLE 1

Information on strains

| Strains | Description |
| --- | --- |
| D452-2 | MATα leu2 ura3 his3 can1 |
| D452-L12 | D452-2 with CS8-LAC12 integration |
| D452-L124 | D452-2 with CS8-LAC12, CS6-LAC4 integration |

TABLE 2

Information on used plasmids

| Plasmids | Description |
| --- | --- |
| p423-pGPD | pSR423-pTDH3-tCYC1 |
| p425-pGPD | pSR425-pTDH3-tCYC1 |
| pRS423-pGPD-LAC12 | p 82 R7S9423-pGPD harboring LAC12 gene from K. lactis Y-8279 |
| pRS425-pGPD-LAC4 | pR7S9425-pGPD harboring LAC4 gene from K. lactis Y-8279 |
| Cas9-NAT | p414-TEF 1p-Cas9-CYC1t-NAT1 |
| p42K-gCS8 | pRS42K carrying guide RNA for integration at CS8 locus |
| p42H-gCS6 | pRS42H carrying guide RNA for integration at CS6 locus |

TABLE 3

Information on used primers

| Primers | Primer sequences |
| --- | --- |
| LAC12-F | 5'-tctagagcggccgcactagtgccaccatggcagatcattcgagcag-3' (SEQ ID NO: 7) |
| LAC12-R | 5'-tctagagcggccgcgtcgacttaaacagattctgcctctg-3' (SEQ ID NO: 8) |
| LAC4-F | 5'-tctagagcggccgcactagtgccaccatgtcttgccttattcctgagaat-3' (SEQ ID NO: 9) |
| LAC4-R | 5'-tctagagcggccgcgtcgacttattcaaaagcgagatcaaactc-3' (SEQ ID NO: 10) |
| gCS8-U | TGATTCAATCATTCTTATTGgttttagagctagaaatagcaag (SEQ ID NO: 11) |
| gCS8-D | CAATAAGAATGATTGAATCAgatcatttatctttcactgcgga (SEQ ID NO: 12) |
| CS8-IU | caaaattacctacggtaattagtgaaaggccaaaatctaatgttacaataAATTAACCCTCACTAAAGGGA (SEQ ID NO: 13) |
| CS8-ID | gaccgttccatgtgttgtaccagtggtagggttatctcggtagatctGTAATACGACTCACTATAGGGC (SEQ ID NO: 14) |
| CS8-CKU | Agtggaacatagaagggg (SEQ ID NO: 15) |
| CS8-CKD | Taagcagcccagtgaac (SEQ ID NO: 16) |
| gCS6-U | GATACTTATCATTAAGAAAAgttttagagctagaaatagcaag (SEQ ID NO: 17) |
| gCS6-D | TTTTCTTAATGATAAGTATCgatcatttatattcactgcgga (SEQ ID NO: 18) |
| CS6-IU | aacctcgaggagaagttttttttaccccctctccacagatcCAGGAAACAGCTATGACCATG (SEQ ID NO: 19) |
| CS6-ID | taattaggtagaccgggtagatttttccgtaaccttggtgtcTGTAAAACGACGGCCAGT (SEQ ID NO: 20) |
| CS6-CKU | Gtctgccgaaattctgtg (SEQ ID NO: 21) |
| CS6-CKD | Cggtcagaaagggaaatg (SEQ ID NO: 22) |

TABLE 4

1. CS8 region, Chromosome XVI (SEQ ID NO: 25)

. . . <TAGATCTTATACAAAAGCAACTGCGCGCTGTGGTAAAGCTACGGAA
ACAATGTCCTATCTGTGGGAAGGTTTGTTCGAGACCTTCAACACTGAGGA
CTCATTACTTAATACATACGGGAGACACACCTTTCAAATGTACTTGGGAG
CATTGCAACAAATCTTTCAATGTCAAGAGTAACATGTTAAGGCATTTAAG
AACCCATCAAAAGAAAATAGCAAAGAAAAAACATCAGTGA>[[[aagcattgttta
gaatattttgttttcagtgtgattttgatgtaggtgtgacacttttaccaagtaaaatgagtatagatatgtattagttccatataat
atattacatgtagccaacaatcaattttactgacttccgatttttgaatagtgagaggattttgttcgaattataatttctacaag
aaatttgtttgcgaatgcatcagcatttgtaatacggttctatactgccgcacgatacattttattctgtctagttcgtaagacaa
aggaccttttcatttagtacaacgttgccgacacggatgtcttgatgaatctctgtaccaggaattcaattcctgactagtatg
cagttcactatcaaaaaaaaaaaaaaggttaaattggtataatcatggttaaagaacaaacagcctcttttcctctacaaaagt
atgttaaatgtaggtagttcaaattgcggtcacgtatatgccaacgttgttaatatataatgatccattggaacaatgaagttta
cagaagctcaaaattaatgcaagaataattacgtcaagggagtcataacaaactaagaaaacaaaggaatttgactaagttt
gagcgcaatgatatatccatgcttgatattctgattcatacatatcgtttctgtcatttcaatggaagtctttatttatcaattacca
caaccttagtattgtgcttattattggtcaaaaggagttcatgcgctagtgatagtcaacccatgaagtgatt]]]{{{agtgg
aacatagaagggg}}}[[[ataaatttcctatcggataacaaagaaaaaccaggattattgitttaccaccacattttcaaact
ttcccgctgaatttc ctactaccctcatttgaaagaacgctttccactctttaggttggcgttgtatcatcttttcttccattcaatg
caccaagacttaattttgttggttaaactcttattattgtcagtttaaccaa]]]{{caaaattacctacggtaattagtgaaagg
ccaaaatctaatgttacaat}}[[[a]]]{tgattcaatcattcttattg}[[[[cgg]]]]{{agaagctaccgagaagaaccc
taccactggtacaacaagggaacggtc}}[[[tcattgacctcgtgcataaccgggaaggtaacacatgaatatgctgt
gtttgaatc atctccaatccaaactataggaatgaaaaattttttttgggtacaatgtcttctcacaatatcgtattcttggtcagc
aatgtttccaaggatgacagactctttctaagaaaagatttcaagttcaaaatttacataacagtgaactatgcagaaaatttta
cttctagaccacgcatttaacaataatgtttgcccgcaacaataaagtatttggtcgctttaagacgttatc agttattttatgag
aaggtgtttaccattcgtgctcccatactaaaaccaaggggtaaataggacccacatttcgtttctgacagccaacaacgtg
ccactagcaggacagttattggaggtttatattatgtaattattgttagctgataaatgatttacagaaagcgctgat]]]{{{g
ttcactgggctgctta}}}[[[ttcagaatccccacgcatatttacttcaaagagaaagaattttttgatgtaagttttatttgaa
cgtggaactttggcgtggggcatttatggctgctatcacacaaatcgcggagcagagtaccccctggattatataacacaac
tcactaaaatcgctcaaaattgggggggtacgggttagcgcggcagctcatcgagggaacagcacctagtgcacgtttaat
tgatagtatcttcagaacgaaatcaaatttttcgcagtatcatttacgtttcaagaaacttaaagtgtttggagaaattaggaac
gaaaaaaagctactatagaaattgtagcctgtcttcaactgctgtcctcggcttttgacttgcctaagtatatgccgcaatggg
cgataagcgggagtgtcggtcagatctgtggtaaaaaaaagatagcaataaaaaattatgaatttaaacagtagtcttgaatt
taaacaagtgatcttgacttgaatacttccatcaatgagtcgctaaaatgaaaatggctgcacaatctcctccgcatatcttaa
aaggcagcaattagccagttgatcaccctacatttccacagaaacgaaaaagtgtaatagttattttgcggccaatatcgta
agctctagcggtgccttagctttatgattgttgcaagaaagtttgccttttttgactctccttcaggtgtcagtattaacaaacgg
cgttgaatgtttaagttattattttattcatcaaatcgacttggatactttctcggtgatgtcgctaattggattataccattaaggtt
gtcaccagtgtaaaaattttgcatcggtacttgcaactacgtgtgaaggtcaagttactcaacgcaaagaaacgttaacatttt
tacaaattttagctgcagtactatgttttaagtaatccaaagggaactatttgttatatcccagaattatttacattcgtttcttagtt
tcataaacaatgaataccctattgaatggatagaaattctgacttgattttacgagttattattgctgacattagtccaaagacatc
tcagttttgtttcctctacaacccaatgaggaggctagccagggctgtcgcccaaaaaaatagccaataaagcggcaactttt
ctgt]]]<<ATGTCTTGCATTTTTTCCGCTGACTTGGGAGTAGAGTACAGCTGC TABLE 4-continued

```
GCGGAGTCGCGTATTACAAATCTTGTACTTTGCATTCTGTGCATACGTGA

GGAAAAAGCAGCACCTGTTGTGAAAAAAGATAAATTTCTTTTTTTCATTT

TTCTATCCTCAAAGGAAAATCTTTTCTGCGAAATTTCTAGCCGCTCTTCAG

TTTCCGAAGTAAAGTCGCTGAGGGCGAAAAACAACTTTATTTGCCCACAC

GCTGTTATAGGCTTCCAGGGAGCAAAAGCGCAATTGGGAATAAGGTTTC

CTCAATTGAATGGTTTGCTTCGCCTACAGCATTAA>>[[[ccagaaggtaatttgatctct tgtatgtccgctaacagatcttgtccattaattgtttattttcttcaggtaggctgagcccactttgtagtagctccctaccattac tatggccagtagttattggctttgattttactttctatgacaatcccgttgagcaaccttgcgaagggctchtttgaaaaaaag gcgtgggcaagatctctgtat]]] . . .
```

<NNNN>: CDS of functional gene
<<NNNN>>: CDS of not essential protein, or protein with no function (or unknown function)
<<<NNNN>>>: tRNA
[NNNN]: δ sequence
[[[nnnn]]]: Non-coding region
[[[[nnnn]]]]: PAM sequence
{nnnn}: Target sequence for gRNA
{{nnnn}}: Homologous region for integration
{{{nnnn}}}: sequencing primer site

TABLE 5

2. CS6 region, Chromosome VII (SEQ ID NO: 26)

```
[[[ataaaa]]]<<<TGAAACGGACAGGAATTGAACCTGCAACCCTTCGATTGCA

ATCTTATTCCGTGGAATTTCCAAGATTTAATTGGAGTCGAAAGCTCTACC

ATTGAGCCACCGCTTC>>>[[[atcttgaaatatcgaagatataacattttactt]]]{{{gtctgccgaaatt ctgtg}}}[[[tttgctataatgtttgaattagaatctcttaaaatagctactcatacttcttcataactaatccattagtgaccata tgaagtaatcggacgccacacatcattgatgtttcacgatggagaatgataacacactaagtggcattgtgggcaaagtaa gttaaacacctattgctcaaatgatcaacttggtgtttgcacatatacggatgtaagtcatgacattgaaatcataatatgctttc atgataatcatatgagcatgtttaatattactaataaggctgtattctatacttctcttatatagaataagaagatctgcatttattct tgattgacactacagttcaacaattaattaccaacagaattaattactacctatcgttcacaagctactacgttatcatacacaat gtaaaaatatgacacaaaaatggaaaaccgtcatcagatttaatggggctgaaacacaagaattcataatgtgatagaataa tgggtgaagtgtataaagaagaatatataatattactgtgtagaaatatcaatttcccttttgtgagttctcat]]]{{aacctcga ggagaagttttttttacccctctccacagatc}}{gatacttatcattaagaaaa}[[[[tgg]]]]{{gacaccaaggttacgg aaaaatctacccggtctacctaatta}}[[[ctctcttggcgcactagttttccgaaaaaaacaggtaaattcttctttagataa agataaatataaaacttcacagccattcactcacacaaactagtcccttagggtgcgtataatgatctgtacatcttatttctata tatcttaccgtgtatttttttctttttctcaattcttgttcgcaaataaaaagatattcgtgtttgtggaagaacactagttccgttttgta ttcaacctggaaatttacaatagatcttcatcatcgtatgtctaccatgttaatctcccgttaaactgtttcacgttatcaagattat gtcatctattcctgggcgaacataattccttacaaaaacatttgtcattacacaagtgtaaggggtaatgaaaagtaattttgtt acaagtacgcaaaattcgtttatttcaagaaacactaaggatcgt]]]{{{catttccctttctgaccg}}}[[[atgttccttct ttttgctatttttttcccgagtcatctcatcgttttgagtttttcctagtccattaaattgtcaccttactctcggaaaaaagaaacga caaatgctcctagtgccgttttttcgaagcttgaaaaaaaaaattgcaaattatttaattttgctgctaaggagttgaagtaggtg cattccgccttattgatcaccctgttagatttgttgcgatcgttatagtgctagtttgtccattgttgtgtcataaaagatagctttg ggagaaaattca]]]<<TCAAAACAACATATCATCAGCGTTATTACAATTCATTGTC

CTTCCCAAGTTTTTTTGACGTATAATATTATCGCTATCTGACTCATTAGTA

CACAAATACAGATATACAACCTCAAAATCAAAAATGCCTAGAAACCCAT
```

TABLE 5-continued

```
TGAAAAAGGAATATTGGGCAGATGTAGTTGACGGATTCAAGCCGGCTAC

TTCTCCAGCCTTCGAGAATGAAAAAGAATCTACTACATTTGTTACCGAAC

TAACTTCCAAAACCGATTCTGCATTTCCATTAAGTAGCAAGGATTCACCT

GGCATAAACCAAACCACAAACGATATTACCTCTTCAGATCGCTTCCGTCG

TAATGAAGACACAGAGCAGGAAGACAT>>[[[caacaacacca]]]
```

<<NNNN>>: CDS of not essential protein, or protein with no function (or unknown function)
<<<NNNN>>>: tRNA
[[[nnnn]]]: Non-coding region
[[[[nnnn]]]]: PAM sequence
{nnnn}: Target sequence for gRNA
{{nnnn}}: Homologous region for integration
{{{nnnn}}}: sequencing primer site <Example 4> Effect of Intracellular AB Uptake by LAC12

To produce L-AHGol from a substrate AB, first, AB needs to be hydrolyzed into a monosaccharide. However, since L-AHG has not only poor thermal stability but also poor stability even when exposed to a medium for a long period of time, when AB itself is brought into the cell and then hydrolyzed, rather than when AB is hydrolyzed to produce L-AHG outside the cell and then brought into the cell, the denaturation of L-AHG may be prevented. Therefore, to minimize the denaturation of L-AHG, AB is intended to be brought into S. cerevisiae. However, native S. cerevisiae is not able to consume lactose. AB and lactose have very similar structures in which L-AHG and glucose as reducing ends are bonded to D-galactose by a β-1,4-glycosidic bond, respectively. Therefore, it is expected that the parent strain D452-2 used in the present invention will not be able to consume AB. To solve this problem, LAC12 expressing a lactose transporter was taken from Kluyveromyces lactis, which is GRAS yeast known to be able to metabolize lactose well, and introduced into D452-2.

As a result of confirming whether AB was brought into the cells by LAC12 expression in a minimal medium (Verduyn medium) for the constructed strain D452-2-L12 and parent D452-2 as a control (FIGS. 4A-4F), it can be seen that D452-2-L12 intracellularly consumed AB, and thus the concentration of AB in the medium decreased. In this case, interestingly, it can also be seen AB was converted into ABol (FIG. 4A). Since AR expressed by GRE3 is an inherent intracellular enzyme, this result is absolute evidence showing that AB was intracellularly consumed. However, in the case of parent D452-2, the concentration of AB in the medium did not decrease, and ABol was also not detected (FIG. 4D). To confirm the possibility that, when a carbon source that may be consumed by a transporter is provided, AB is consumed together or AB is uptaken into the cell by producing energy from the carbon source, about 10 g/L of glucose and galactose, which are representative carbon sources, was provided, and then AB consumption experiments were performed for D452-2-L12 and parent D452-2 as a control. As a result, both when glucose (FIG. 4B) was provided and when galactose (FIG. 4C) was provided, only D452-2-L12 was able to consume AB and produced ABol. On the other hand, parent D452-2 did not consume both glucose (FIG. 4E) and galactose (FIG. 4F). Therefore, D452-2-L12 was able to consume AB by LAC12.

<Example 5> AB Hydrolysis Effect of LAC4

AB as a substrate for producing L-AHGol is intracellularly uptaken and then needs to be hydrolyzed to intracellularly produce L-AHG and D-Gal. As described above, native S. cerevisiae is unable to intracellularly consume lactose, and thus hydrolysis does also not occur. Therefore, to apply β-galactosidase which is derived from K. lactis known to be able to metabolize lactose well and is thus able to hydrolyze lactose, based on the structural similarity of lactose and AB, a LAC4 gene expressing the β-galactosidase was introduced into D452-2-L12.

The AB hydrolysis ability of LAC4 was examined for the constructed strain D452-2-L124 and controls D452-2-L12 and parent D452-2. Since a method of verifying AB hydrolysis is to verify the enzymatic reaction in the cell, a protein, that is, a coenzyme, obtained by growth, collection, and lysis of each cell was used to measure the AB hydrolysis ability. More specifically, each strain was allowed to grow in a YP medium, which is a nutrient broth containing 20 g/L of glucose, at 30° C. and centrifuged in the mid-exponential growth phase at 3,000 g for 10 minutes to collect cells. The collected cells were released with a 20 mM Tris-HCl (pH 7.4) buffer and then lyzed using a sonicator. The lyzed cells were centrifuged at 4° C. and 10,000 g for 10 minutes. The resultant was analyzed by BCA protein concentration quantification to measure the concentration of a coenzyme.

Enzymatic reaction conditions for AB hydrolysis by LAC4 were as follows. AB and lactose as a positive control were used as substrates in the experiment. Each substrate with a concentration of 2 g/L and a coenzyme at 0.5 g/L were reacted in a sodium acetate (pH 6.0) buffer at 30° C. As shown in FIG. 5, it was confirmed that AB was best hydrolyzed in the coenzyme obtained from the D452-2-L124 strain. However, AB was hardly hydrolyzed in the coenzymes obtained from strains not expressing LAC4, D452-2-L12 and parent D452-2. This result coincides with a result for lactose which is a positive control. However, AB was found to be less reactive to β-galactosidase expressed by LAC4 than lactose. This is due to a structural difference between AB and lactose. In this way, it is expected that AB brought into the cell by LAC12 will be hydrolyzed by LAC4.

<Example 6> Cell Growth Inhibition Effect According to Concentration of Substrate AB As described above, to produce L-AHGol, AB needs to be brought into the cell and then hydrolyzed to produce L-AHG. However, L-AHG has been reported to have an antibacterial effect against Streptococcus mutans. In industrialization, the addition of a high concentration of substrate is important in terms of not only increasing the final concentration of a desired reaction product but also reducing process costs such as reducing a reactor, using a smaller amount of water, and the like. However, when the growth of the host *S. cerevisiae* is inhibited by the substrate AB, a high concentration of AB will not be added. Therefore, the effect of inhibiting the growth of genetically engineered D452-2-L124 and controls, D452-2-L12 and parent D452-2, according to various concentrations of AB was confirmed.

An experiment for confirming the growth inhibition effect is as follows. Each strain was cultured in a minimal medium (Verduyn medium) at 30° C. and 300 rpm by providing 20 g/L of glucose as a carbon source and varying an AB concentration at 0, 10, 20, and 50 g/L. As a result, as the AB concentration increased, the specific growth rate of D452-2-L124 most sharply decreased (FIG. 6A). Also, the specific growth rate of D452-2-L12 decreased as the AB concentration increased. However, the specific growth rate of parent D452-2 was not affected until the AB concentration was 20 g/L, unlike D452-2-L124 and D452-2-L12. When the AB concentration was 50 g/L, D452-2-L124 and D452-2-L12 did not grow, but parent D452-2 slowly grew afterward. This is because an increase in AB concentration causes a glucose (carbon source) consumption rate to be decreased (FIG. 6B). The glucose consumption rate of each strain also showed a tendency similar to the specific growth rate shown in FIG. 6A.

It is not appropriate that low cell-density fermentation is used due to inhibition of the growth of the genetically engineered strain D452-2-L124 as the concentration of the substrate AB increases. Therefore, to solve this problem, high cell-density culture was considered.

AB was almost completely consumed in 49 hours, and 9.25 g/L of L-AHGol was produced. However, unlike the condition of AB with a concentration of 10 g/L, AB was converted into ABol at the beginning of fermentation, but ABol was not completely hydrolyzed and remained in an amount of 0.33 g/L as a by-product even though the fermentation was terminated, and 0.33 g/L of galactitol (Galol) which is a sugar alcohol of Gal was produced. In the case of further increasing the AB concentration (45 g/L) (FIG. 7C), AB was consumed to produce 18.62 g/L of L-AHGol for about 84 hours. However, by-products, ABol and Galol, were produced in large amounts of 1.41 g/L and 1.46 g/L, respectively, compared to those under the preceding condition. Under the condition of AB with a concentration of 90 g/L (FIG. 7D), about 43.92 g/L of AB was consumed for 84 hours, and 12.91 g/L of L-AHGol was produced. In this case, by-products, ABol and Galol, were also produced in large amounts of 2.24 g/L and 0.98 g/L, respectively, compared to those under the condition of 20 g/L or less. In this case, interestingly, the yield of L-AHGol produced as the AB concentration rapidly increased was decreased (Table 6). In particular, under the condition of 90 g/L, L-AHGol was produced with a very low yield of 0.29 g/g AB consumed. The yield of by-products, ABol and Galol, also increased as the AB concentration increased, except for the condition of 90 g/L. When provided with a carbon source, *S. cerevisiase* is known to typically produce ethanol, glycerol, and acetic acid, but these products were not finally produced.

Based on the result, since the L-AHGol yield was high until the AB concentration was 20 g/L, a high concentration of AB was applied through fed-batch saccharification so as to produce a high concentration and high yield of L-AHGol.

TABLE 6

Concentration and yield of L-AHGol, ABol, and Galol by high cell-density culture according to AB concentration

| AB concentration (g/L) | L-AHGol | | ABol | | Galol | |
|---|---|---|---|---|---|---|
| | Titer (g/L) | Yield (g/g AB consumed) | Titer (g/L) | Yield (g/g AB consumed) | Titer (g/L) | Yield (g/g AB consumed) |
| 10 | 4.62 ± 0.07 | 0.47 ± 0.01 | 0.10 ± 0.02 | 0.01 ± 0.00 | 0.00 ± 0.00 | 0.00 ± 0.00 |
| 20 | 9.25 ± 0.00 | 0.48 ± 0.00 | 0.33 ± 0.00 | 0.02 ± 0.00 | 0.33 ± 0.04 | 0.02 ± 0.00 |
| 45 | 18.62 ± 0.05 | 0.42 ± 0.00 | 1.41 ± 0.06 | 0.03 ± 0.00 | 1.46 ± 0.10 | 0.03 ± 0.00 |
| 90 | 12.91 ± 0.45 | 0.29 ± 0.01 | 2.24 ± 0.14 | 0.05 ± 0.00 | 0.98 ± 0.09 | 0.02 ± 0.00 |

<Example 7> High Cell-Density Culture for Producing L-AHGol According to AB Concentration Since the growth of D452-2-L124 is inhibited as the concentration of the substrate AB increases, this example was attempted to overcome the growth inhibition through high cell-density culture. An experiment method is as follows. D452-2-L124 with a high concentration of 6 g/L was used, and the substrate AB was added so that the concentration thereof was about 10, 20, 45, and 90 g/L. Fermentation was performed in a minimal medium (Verduyn medium) at 30° C. and 300 rpm. As a result (see FIGS. 7A-7D and Table 4), under the condition of AB with a concentration of 10 g/L, AB was completely consumed in 36 hours, and 4.62 g/L of L-AHGol was produced. In the process of consuming AB, AB was initially converted into ABol, but the final amount of ABol was 0.10 g/L as ABol was almost completely hydrolyzed (FIG. 7A). Under the condition of AB with a concentration of 20 g/L (FIG. 7B), <Example 8> Production of High Concentration of Substrate AB from High Concentration of Agarose Through Phosphoric Acid Hydrolysis To produce L-AHGol from red algae, a substrate AB was produced from agarose. As described above, the addition of a high concentration of substrate in the process is important in several ways. Reaction conditions for producing a high concentration of AB are as follows. A high concentration (20% (w/w)) of agarose was allowed to react with 2% (w/v) phosphoric acid at 95° C. for 120 minutes. For example, 90 g of agarose was allowed to react with 360 mL so that the final concentration of agarose was 20% (w/w).

As a result, AB was finally produced with a high concentration of 128.99 g/L. To use the agarose hydrolysate as a substrate, calcium hydroxide ($Ca(OH)_2$) was used to neutralize and remove the phosphoric acid. The resultant was used as a substrate for subsequently producing L-AHGol (FIG. 8).

<Example 9> Production of L-AHGol from Agarose Hydrolysate Through Fed-Batch Culture Using Fermentor To examine the possibility that L-AHGol may be mass-produced from red algae, a fermentor was used. Based on the above-described results, to produce a high concentration and high yield of L-AHGol using a high concentration of agarose hydrolysate as a substrate, first, D452-2-L124 was subjected to high cell-density culture. Second, an agarose hydrolysate containing a high-concentration (128.99 g/L) of AB was subjected to fed-batch culture five times. Finally, pre-cultivation was performed to minimize a by-product Galol, and strains were designed using D-Gal as a carbon source for increasing a cell concentration so that the strains adapt to D-Gal and thus consume the same well. Operating conditions of the fermentor were as follows: a reaction volume in a 1 L fermentor was 450 mL, a minimal medium (Verduyn medium) was used as a medium, and 30° C. and pH 6.0 were set. Each of 5 N NaOH and HCl was used for pH control. A stirring rate was set at 500 rpm, and an aeration rate was set to 2 vvm.

As shown in FIG. 9, by adding 20 to 30 g/L D-Gal as a carbon source in a fed-batch manner, cultivation was performed for about 30 hours until a cell concentration reached 23.85 g/L which is about 4.33 times higher than the initial cell concentration of 5.51 g/L. In this case, as D-Gal was consumed, by-products such as ethanol, glycerol, and acetic acid were produced. Particularly, glycerol was produced in an amount of 7.56 g/L. After 30 hours, an agarose hydrolysate was dividedly added five times. As a result, AB contained in the agarose hydrolysate was hydrolyzed and thus converted well into L-AHGol. Finally, a high concentration and high yield of L-AHGol was successively produced from 41.18 g/L and 0.48 g/g AB. As fermentation proceeded, the initially produced ethanol, glycerol, and acetic acid were consumed again in the cell and thus hardly produced, and ABol and Galol were produced in very small amounts of 0.68 g/L and 1.18 g/L, respectively. This is very favorable for subsequently separating and purifying L-AHGol.

<Example 10> Separation and Purification of L-AHGol from Fermentation Product Using Size Exclusion Chromatography To separate and purify L-AHGol from the product of fermentation, size exclusion chromatography was used. Sephadex G-10 (GE Healthcare) was used as a resin, and distilled water was used as a mobile phase.

As shown in FIG. 10, since other by-products were hardly produced other than an oligosaccharide with a high degree of polymerization, which remained unhydrolyzed after agarose was hydrolyzed by phosphoric acid, and medium components used in fermentation, L-AHGol was easily separated by size exclusion chromatography. In addition, since distilled water was used as a mobile phase, there is no need for a subsequent process, and thus a process is simple.

<Example 11> Thermal Stability of L-AHG, AB, L-AHGol, and ABol

To confirm whether L-AHGol and L-ABol, which were produced by fermentation and separated by size exclusion chromatography, are actually stable against heat, L-AHG and AB were experimentally compared. The experiment was performed by measuring the degree of denaturation of each substance over time at 4, 25, 50, and 70° C.

As shown in FIGS. 11A-11D, L-AHG and AB were denatured over time at 50° C. or more, but L-AHGol and ABol were very stable without being denatured even at 70° C.

The invention claimed is:

1. A method of producing a sugar alcohol using agarobiose as a substrate, comprising
   fermenting a recombinant yeast in the presence of agarobiose and carbon source,
   wherein the recombinant yeast expresses a gene encoding aldose reductase (AR) and a gene encoding lactose permease.

2. The method of claim 1, comprising:
   subjecting the recombinant yeast to high cell-density culture;
   producing a high concentration of agarobiose as a substrate; and
   subjecting the high cell-density cultured recombinant yeast to fed-batch culture using the produced high concentration of agarobiose and one or more of D-Gal, D-Glc, and lactose as a carbon source to induce fermentation.

3. The method of claim 1, wherein the recombinant yeast further comprises a gene encoding β-galactosidase.

4. The method of claim 1, wherein the sugar alcohol is agarobititol (ABol).

5. The method of claim 3, wherein the sugar alcohol is one or more of agarobititol and 3,6-anhydro-L-galactitol (L-AH-Gol).

6. The method of claim 1, wherein the gene encoding aldose reductase is a GRE3 gene derived from *Saccharomyces cerevisiae*.

7. The method of claim 1, wherein the gene encoding lactose permease is a LAC12 gene isolated from *Kluyveromyces lactis* (NRRL: Y-8279) and transformed into the recombinant yeast.

8. The method of claim 3, wherein the gene encoding lactose permease and the gene encoding β-galactosidase are a LAC12 gene and a LAC4 gene which are isolated from *Kluyveromyces lactis* (NRRL: Y-8279) and transformed into the recombinant yeast, respectively.

9. The method of claim 6, wherein the GRE3 gene is represented by a base sequence set forth in SEQ ID NO: 1.

10. The method of claim 7, wherein the LAC12 gene is represented by a base sequence set forth in SEQ ID NO: 2.

11. The method of claim 8, wherein the LAC4 gene is represented by a base sequence set forth in SEQ ID NO: 3.

12. The method of claim 1, wherein the recombinant yeast is one or more of *Saccharomyces cerevisiae, Pichia pastoris, Schizosaccharomyces, Kluyveromyces lactis, Neurospora crassa, Yarrowia lipolytica, Pichia angusta, Candida boidinii*, and *Blastobotrys adeninivorans*.

* * * * *